US010071101B2

(12) United States Patent
Mold

(10) Patent No.: US 10,071,101 B2
(45) Date of Patent: *Sep. 11, 2018

(54) USE OF CINNABARINIC ACID AS A MODULATOR OF IMMUNE RESPONSE IN AUTOIMMUNE DISORDERS

(71) Applicant: The Regents of the University of California, Oakland, CA (US)

(72) Inventor: Jeffrey Eron Mold, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/339,609

(22) Filed: Oct. 31, 2016

(65) Prior Publication Data

US 2017/0143727 A1 May 25, 2017

Related U.S. Application Data

(63) Continuation of application No. 13/579,893, filed as application No. PCT/US2011/025906 on Feb. 23, 2011, now Pat. No. 9,486,457.

(60) Provisional application No. 61/307,358, filed on Feb. 23, 2010.

(51) Int. Cl.
*A61K 31/538* (2006.01)

(52) U.S. Cl.
CPC ................ *A61K 31/538* (2013.01)

(58) Field of Classification Search
None
See application file for complete search history.

(56) References Cited

U.S. PATENT DOCUMENTS

| | | | |
|---|---|---|---|
| 4,053,460 | A | 10/1977 | Apple et al. |
| 6,716,883 | B1 | 4/2004 | Casper et al. |
| 9,486,457 | B2 | 11/2016 | Mold |
| 2003/0069443 | A1 | 4/2003 | Kamikawa et al. |
| 2005/0250753 | A1 | 11/2005 | Fink et al. |
| 2013/0035333 | A1 | 2/2013 | Mold |

FOREIGN PATENT DOCUMENTS

| | | |
|---|---|---|
| EP | 0502661 A2 | 9/1992 |
| WO | 2011106408 A1 | 9/2011 |

OTHER PUBLICATIONS

Nakagome et al., High Expression of IL-22 Supresses Antigen-Induced Immune Responses and Eosinophilic Airway Inflammation via an IL-10-Associated Mechanisms, The Journal of Immunology, J Immunol 2011; 187:5077-5089.*
Pan et al., "Emerging role of interleukin-22 in autoimmune diseases," Cytokine Growth Factor Rev. Feb. 2013; 24(1): 51-57.*
Sabat et al., "Therapeutic opportunities of the IL-22-IL-22R1 system," Nature Reviews Drug Discovery, vol. 13, Jan. 2014.*
Song et al., "Different levels of circulating Th22 cell and its related molecules in Graves' disease and Hashimoto's thyroiditis," Int J Clin Exp Pathol 2014;7(7): 4024-4031.*
Cobleigh et al., "Protective and Pathological Properties of IL-22 in Liver Disease," The American Journal of Pathology, vol. 182, No. 1, Jan. 2013.*
Blue Emerald Article, http://www.esmeraldazul.com/en/blog/mucosa-inflammation-many-diseases-are-ultimately-just-one-2-2/- date accessed Dec. 13, 2017.*
Gilenya General Prescribing Information—Novartis Pharma, http://www.phrama.us.novartis.com/cs/www.pharma.us.novartis.com/product/pi/pdf/gilenya.pdf, 2013, 22 pages.
Cinnabarinic acid, Compound Summary (CID 114918). Pubchem http://pubchem.ncbi.nlm.nih.gov/summary/summary.cgisid=691858&vIewopt=PubChem, Jun. 24, 2005, pp. 1-4.
Albers et al., Cyclodextrin Derivatives in Pharmaceutics, Critical Reviews in Therapeutic Drug Carrier Systems, vol. 12, No. 4, 1995, pp. 311-337.
Belladonna et al., Kynurenine Pathway Enzymes in Dendritic Cells Initiate Tolerogenesis in the Absence of functional IDO, J Immunol, vol. 177, No. 1, 2006, pp. 130-137.
Besteman et al., Tetrachlorodibenzo-p-Dioxin (TCDD) Inhibits Differentiation and Increases Apoptotic Cell Death of Precursor T-Cells in the Fetal Mouse Thymus, Journal of Immunotoxicology, vol. 2, 2005, pp. 107-114.
Choi et al., FTY720 (fingolimod) efficacy in an animal model of multiple sclerosis requires astrocyte sphingosine 1-phosphate receptor 1 (S1 P1) modulation, PNAS, vol. 108, No. 2, 2011, pp. 751-756.
Chun et al., Mechanism of Action of Oral Fingolimod (FTY720) in Multiple Sclerosis, Clin. Neuropharmacol., vol. 33, No. 2, 2010, pp. 91-101.
Den Braber et al., Maintenance of Peripheral Naive T Cells Is Sustained by Thymus Output in Mice but Not Humans, Immunity, vol. 36, Feb. 24, 2012, pp. 288-297.
Denison et al., Activation of the Aryl Hydrocarbon Receptor by Structurally Diverse Exogenous and Endogenous Chemicals, Annu. Rev. Pharmacol. Toxicol., vol. 43, 2003, pp. 309-334.
Dzhagalov et al., Elimination of Self-Reactive T Cells in the Thymus: A Timeline for Negative Selection, PLoS Biology, vol. 11, No. 5, May 2013, pp. 1-14.
Foster et al., Brain Penetration of the OralImmunomodulatory Drug FTY720 and Its Phosphorylation in the Central Nervous System during Experimental Autoimmune Encephalomyelitis: Consequences for Mode of Action in Multiple Sclerosis, The Journal of Pharmacology and Experimental Therapeutics, vol. 323, No. 2, 2007, pp. 469-476.
Gasperini et al., Development of oral agent in the treatment of multiple sclerosis: how the first available oral therapy, fingolimod will change therapeutic paradigm approach, Drug Design, Development and Therapy, vol. 6, 2012, pp. 175-186.
Gelderman et al., Macrophages suppress T cell responses and arthritis development in mice by producing reactive oxygen species, The Journal of Clinical Investigation, vol. 117, No. 10, 2007, pp. 3020-3028.
Gonsette, Advances in Treating Multiple Sclerosis, Touch Briefings, 2007, pp. 18-20.

(Continued)

*Primary Examiner* — Jared Barsky
(74) *Attorney, Agent, or Firm* — Kilpatrick Townsend & Stockton

(57) ABSTRACT

The present invention provides compounds and methods for preventing and treating an immune disorder in a subject.

7 Claims, 15 Drawing Sheets

(56) References Cited

OTHER PUBLICATIONS

Hayashi et al., 3-Hydroxyanthranilic acid inhibits PDK1 activation and suppresses experimental asthma by inducing T cell apoptosis, PNAS, vol. 104, No. 47, Nov. 20, 2007, pp. 18619-18624.
Hebb et al., Targeting Apoptosis to Treat Multiple Sclerosis, Current Drug Discovery Technologies, vol. 5, 2008, p. 75-77.
Hiramatsu, Cinnabarinic Acid Generated From 3-Hydroxyanthranilic Acid Strongly Induces Apoptosis in Thymocytes Through the Generation of Reactive Oxygen Species and the Induction of Caspase, Journal of Cellular Biochemistry, vol. 103, No. 1, 2008, pp. 42-53.
Hultqvist et al., Enhanced autoimmunity, arthritis, and encephalomyelitis in mice with a reduced oxidative burst due to a mutation in the Ncf1 gene, PNAS, vol. 101, No. 34, 2004, pp. 12646-12651.
Hultqvist et al., Lack of Reactive Oxyen Species Breaks T Cell Tolerance to Collagen Type II and Allows Development of Arthritis in Mice, J. Immunol., vol. 179, No. 3, 2007, pp. 1431-1437.
Jackson et al., Fingolimod modulates microglial activation to augment markers of remyelination, Journal of Neuroinflammation, vol. 8, No. 76, 2011, 12 pages.
Jasperson et al., Inducing the tryptophan catabolic pathway, indoleamine 2,3-dioxygenase (I DO), for suppression of graft-versus-host disease (GVHD) lethality, Blood, vol. 114, No. 24, Dec. 3, 2009, pp. 5062-5070.
Johnson et al., Targeting the immunoregulatory indoleamine 2,3 dioxygenase pathway in immunotherapy, Immunotherapy, vol. 1, No. 4, Jul. 1, 2009, pp. 645-661.
Kamath et al., Characterization of Phenotypic Alterations Induced by 2,3,7,8-Tetrachlorodibenzo-p-dioxin of thymocytes in Vivo and Its Effect on Apoptosis, Toxicology and Applied Pharmacology, vol. 150, 1998, pp. 117-124.
Mellor et al., Cells Expressing Indoleamine 2,3-Dioxygenase Inhibit T Cell Responses, J. Immunol, vol. 168, No. 8, 2002, pp. 3771-3776.
Mezrich et al., An Interaction between Kynurenine and the Aryl Hydrocarbon Receptor Can Generate Regulatory T Cells, The Journal of Immunology, vol. 185, No. 6, Sep. 15, 2010, pp. 3190-3198.
Nagahara et al., T cell selective apoptosis by a novel immunosuppressant, FTY720, is closely regulated with Bcl-2, British Journal of Pharmacology, vol. 137, 2002, pp. 953-962.
Nagai et al., Constitutive activation of the aryl hydrocarbon receptor in T-lineage cells induces thymus involution independently of the Fas/Fas ligand signaling pathway, International Immunopharmacology, vol. 6, 2006, pp. 279-286.
International Application No. PCT/US2011/025906, International Search Report and the Written opinion dated May 26, 2011, 6 pages.
Platten et al., Treatment of autoimmune neuroinflammation with a synthetic tryptophan metabolite, Science, vol. 310, Nov. 4, 2005, pp. 850-855.
Potteck et al., Phosphorylation of the Immunomodulator FRY720 Inhibits Programmed Cell Death of Fibroblasts via the S1 P3 Receptor Subtype and Bcl-2 Activation, Cell Physiol Biochem, vol. 26, 2010, pp. 67-78.
Quintana et al., Control of Treg and T H17 cell differentiation by the aryl hydrocarbon receptor, Nature, vol. 453, May 2008, pp. 65-71.
Schuchardt et al., Pharmacological relevance and potential of sphingosine 1-phosphate in the vascular system, British Journal of Pharmacology, vol. 163, 2011, pp. 1140-1162.
Serpero et al., Fingolimod Modulates Peripheral Effector and Regulatory T Cells in MS Patients, J. Neuroimmune Pharmacol, vol. 8, 2013, pp. 1106-1113.
Silverstone et al., Dexamethasone, beta-Estradiol, and 2,3,7,8-Tetrachlorodibenzo-p-dioxin Elicit Thymic Atrophy through Different Cellular Targets, Toxicology and Applied Pharmacology, vol. 126, 1994, pp. 248-259.
Takabe et al., Inside-Out Signaling of Sphingosine-1-Phosphate: Therapeutic Targets, Pharmacological Reviews, vol. 60, No. 2, 2008, pp. 181-195.
Trifari et al., Identification of a human helper T cell population that has abundant production of interleukin 22 and is dinstinct from Tw17, T H1 and T H2 cells, Nature Immunology, vol. 10, No. 8, Aug. 2009, pp. 864-872.
Veldhoen et al., Natural agonists for aryl hydrocarbon receptor in culture medium are essential for optimal differentiation of Th17 T cells, J Exp Med, vol. 206, No. 1, 2009, pp. 43-49.
Veldhoen et al., The aryl hydrocarbon receptor links T H17-cell-mediated autoimmunity to environmental toxins, Nature, vol. 453, May 1, 2008, pp. 106-109.
Weiner, Immunosuppressive treatment in multiple sclerosis, Journal of the Neurological Sciences, vol. 223, No. 1, Aug. 2004, pp. 1-11.
Esser, et al., "The aryl hydrocarbon receptor in immunity," *Trends in Immunology*, (2009) 30(9):447-454.
O'Donnell, et al., "The Anti-Inflammatory Drug Leflunomide Is an Agonist of the Aryl Hydrocarbon Receptor," *PLoS One*, Oct. 2010, 5(10)e13128:1-13.
Joshi et al., "Aryl Hydrocarbon Receptor—Dependent Stanniocalcin 2 Induction by Cinnabarinic Acid Provides Cytoprotection against Endoplasmic Reticulum and Oxidative Stress," J Pharmacol Exp Ther (Apr. 2015) 353:201-212.
Kawai et al., "Indigo Naturalis ameliorates murine dextran sodium sulfateinduced colitis via aryl hydrocarbon receptor activation," J Gastroenterol (2017) 52:904-919.
Lamas et al., "CARD9 impacts colitis by altering gut microbiota metabolism of tryptophan into aryl hydrocarbon receptor ligands," Nat Med. (Jun. 2016),MON 22(6): 598-605.
Monteleone et al., "Aryl Hydrocarbon Receptor-Induced Signals Up-regulate IL-22 Production and Inhibit Inflammation in the Gastrointestinal Tract," Gastroenterology (2011), 141:237-248.
Monteleone et al., "The aryl hydrocarbon receptor in inflammatory bowel disease: linking the environment to disease pathogenesis," Curr Opin Gastroenterology (Jul. 2012) 28(4)310-313.
Sugimoto et al., "IL-22 ameliorates intestinal inflammation in a mouse model of ulcerative colitis," The Journal of Clinical Investigation (Feb. 2008), 118(2):534-544.
Wang et al., "Immune mechanisms of Concanavalin A model of autoimmune hepatitis," World J Gastroenterol (Jan. 14, 2012) 18(2):119-125.
Zelante et al., "Tryptophan Catabolites from Microbiota Engage Aryl Hydrocarbon Receptor and Balance Mucosal Reactivity via Interleukin-22," Immunity (Aug. 22, 2013), 39:372-385.
Zenewicz et al, "Innate and adaptive interleukin-22 protects mice from inflammatory bowel disease," Immunity (Dec. 19, 2008), 29(6):947-957.

* cited by examiner

|      | Incidence | mean day of onset | mean severity |
|------|-----------|-------------------|---------------|
| DMSO | 9/10      | 12.2              | 2.65          |
| CA   | 6/10      | 12.6              | 1.25          |

USE OF CINNABARINIC ACID AS A MODULATOR OF IMMUNE RESPONSE IN AUTOIMMUNE DISORDERS

CROSS-REFERENCES TO RELATED APPLICATIONS

The present application claims priority to U.S. Provisional Patent Application No. 61/307,358, filed on Feb. 23, 2010, which is incorporated by reference in its entirety.

STATEMENT AS TO RIGHTS TO INVENTIONS MADE UNDER FEDERALLY SPONSORED RESEARCH AND DEVELOPMENT

This invention was made with Government support under Grant Nos. DP1 OD000329 and R37 AI40312 awarded by the National Institutes of Health. The Government has certain rights in the invention.

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Ligation of Aryl Hydrocarbon Receptor (AHR) by environmental toxins has been linked to numerous clinically relevant settings ranging from autoimmune disorders to cancers. Therefore, there is a need to identify and/or to develop compounds that are capable of treating these disorders related to Aryl Hydrocarbon Receptor (AHR). The present invention satisfies this and other needs.

BRIEF SUMMARY OF THE INVENTION

The present invention provides compounds and methods for preventing and treating an immune disorder in a subject.

In some embodiments, the methods comprise administering to the subject compounds of the present invention in an amount sufficient prevent or treat an autoimmune disorder such as multiple sclerosis, myasthenia gravis, Guillan-Barre syndrome (antiphospholipid syndrome), systemic lupus erytromatosis, Behcet's syndrome, Sjogrens syndrome, rheumatoid arthritis, Hashimoto's disease/hypothyroiditis, primary biliary cirrhosis, mixed connective tissue disease, chronic active hepatitis, Graves' disease/hyperthyroiditis, scleroderma, chronic idiopathic thrombocytopenic purpura, diabetic neuropathy and septic shock.

In one embodiment, the present invention provides a method of treating an autoimmune disorder, the method comprising administering to a subject in need thereof, a therapeutically effective amount of a compound of formula Ib:

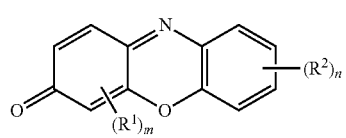

wherein each $R^1$ is independently selected from the group consisting of hydrogen, $-NH_2$, $C_{1-6}$ alkylamine, $-CO_2H$, $C_{1-6}$ alkyl-$CO_2H$, and $C_{0-6}$ alkyl-$C(O)NH_2$ and each $R^2$ is independently selected from the group consisting of hydrogen, $-NH_2$, $C_{1-6}$ alkylamine, $-CO_2H$, $C_{1-6}$ alkyl-$CO_2H$, and $C_{0-6}$ alkyl-$C(O)NH_2$. Subscript m of formula 1b is an integer from 1 to 3, and subscript n is an integer from 1 to 4. The compounds of formula 1b include salts and isomers thereof.

In another embodiment, the present invention provides a method of modulating Aryl Hydrocarbon Receptor activity by administering a compound of formula Ib:

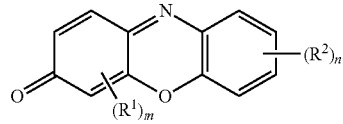

wherein each $R^1$ is independently selected from the group consisting of hydrogen, $-NH_2$, $C_{1-6}$ alkylamine, $-CO_2H$, $C_{1-6}$ alkyl-$CO_2H$, and $C_{0-6}$ alkyl-$C(O)NH_2$ and each $R^2$ is independently selected from the group consisting of hydrogen, $-NH_2$, $C_{1-6}$ alkylamine, $-CO_2H$, $C_{1-6}$ alkyl-$CO_2H$, and $C_{0-6}$ alkyl-$C(O)NH_2$. Subscript m of formula 1b is an integer from 1 to 3, and subscript n is an integer from 1 to 4. The compounds of formula 1b include salts and isomers thereof.

In other embodiments, the methods comprise administering Cinnabarinic Acid.

DETAILED DESCRIPTION OF THE INVENTION

I. General

Figure 1:
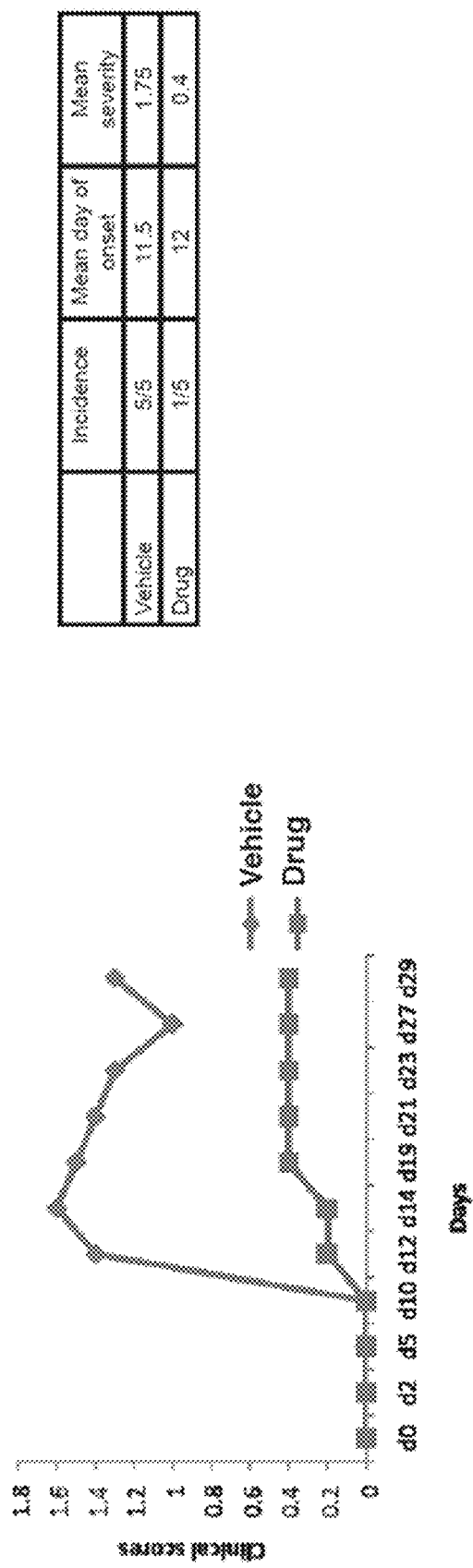
FIG. 1 illustrates that Cinnabarinic Acid inhibits the development of experimental allergic encephalomyelitis (EAE) in C57BL/6 mice with a single dose given at the time that MOG peptide and CFA were injected—Day 0.

The present invention provides compounds and methods for preventing and treating an autoimmune disorder in a subject. The methods comprising administering to the subject compounds of the present invention in an amount sufficient prevent or treat an autoimmune disorder such as multiple sclerosis, myasthenia gravis, Guillan-Barre syndrome (antiphospholipid syndrome), systemic lupus erytromatosis, Behcet's syndrome, Sjogrens syndrome, rheumatoid arthritis, Hashimoto's disease/hypothyroiditis, primary biliary cirrhosis, mixed connective tissue disease, chronic active hepatitis, Graves' disease/hyperthyroiditis, scleroderma, chronic idiopathic thrombocytopenic purpura, diabetic neuropathy and septic shock. The methods also comprise administering compounds of the present invention to modulate AHR activity.

II. Definitions

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together.

The term "lower" referred to above and hereinafter in connection with organic radicals or compounds respectively defines a compound or radical which can be branched or unbranched with up to and including 7, preferably up to and including 4 and (as unbranched) one or two carbon atoms.

As used herein, the term "alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of —$(CH_2)_n$—, where n is 1, 2, 3, 4, 5 or 6. Alkylene groups include, but are not limited to, methylene, ethylene, propylene, isopropylene, butylene, isobutylene, sec-butylene, pentylene and hexylene.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2m'+1), where m' is the total number of carbon atoms in such radical. R', R" and R'" each independently refer to hydrogen, unsubstituted ($C_1$-$C_8$)alkyl and heteroalkyl, unsubstituted aryl, aryl substituted with 1-3 halogens, unsubstituted alkyl, alkoxy or thioalkoxy groups, or aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). Preferably, the substituted alkyl and heteroalkyl groups have from 1 to 4 substituents, more preferably 1, 2 or 3 substituents. Exceptions are those perhalo alkyl groups (e.g., pentafluoroethyl and the like) which are also preferred and contemplated by the present invention.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

As used herein, the term "alkoxy" refers to alkyl group having an oxygen atom that either connects the alkoxy group to the point of attachment or is linked to two carbons of the alkoxy group. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "haloalkoxy" group.

As used herein, the term "alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can also have from 2 to 3, 2 to 4, 2 to 5, 3 to 4, 3 to 5, 3 to 6, 4 to 5, 4 to 6 and 5 to 6 carbons. The alkenyl groups is typically monovalent, but can be divalent, such as when the alkenyl group links two moieties together.

As used herein, the term "alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene.

As used herein, the term "alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can also have from 2 to 3, 2 to 4, 2 to 5, 3 to 4, 3 to 5, 3 to 6, 4 to 5, 4 to 6 and 5 to 6 carbons. The alkynyl groups is typically monovalent, but can be divalent, such as when the alkynyl group links two moieties together.

As used herein, the term "alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, isopropynylene, butynylene, sec-butynylene, pentynylene and hexynylene.

As used herein, the term "alkyl amine" refers to an alkyl groups as defined within, having one or more amino groups. The amino groups can be primary, secondary or tertiary. The alkyl amine can be further substituted with a hydroxy group. Alkyl amines useful in the present invention include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group. One of skill in the art will appreciate that other alkyl amines are useful in the present invention.

As used herein, the term "halogen" refers to fluorine, chlorine, bromine and iodine.

As used herein, the term "haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, flouromethyl, 1,2,3,4,5-pentafluoro-phenyl, etc. The term "perfluoro" defines a compound or radical which has at least two available hydrogens substituted with fluorine. For example, perfluorophenyl refers to 1,2,3,4,5-pentafluorophenyl, perfluoromethane refers to 1,1,1-trifluoromethyl, and perfluoromethoxy refers to 1,1,1-trifluoromethoxy.

As used herein, the term "halo-alkoxy" refers to an alkoxy group having at least one halogen. Halo-alkoxy is as defined for alkoxy where some or all of the hydrogen atoms are substituted with halogen atoms. The alkoxy groups can be substituted with 1, 2, 3, or more halogens. When all the hydrogens are replaced with a halogen, for example by fluorine, the compounds are per-substituted, for example, perfluorinated. Halo-alkoxy includes, but is not limited to, trifluoromethoxy, 2,2,2,-trifluoroethoxy, perfluoroethoxy, etc.

As used herein, the term "cycloalkyl" refers to a saturated or partially unsaturated, monocyclic, fused bicyclic or bridged polycyclic ring assembly containing from 3 to 12 ring atoms, or the number of atoms indicated Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, C$_{3-8}$cycloalkyl includes cyclopropyl, cyclobutyl, cyclopentyl, cyclohexyl, cyclooctyl, and norbornane.

As used herein, the term "cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

As used herein, the term "heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

As used herein, the term "heterocyclalkylene" refers to a heterocyclalkyl group, as defined above, linking at least two other groups. The two moieties linked to the heterocyclalkylene can be linked to the same atom or different atoms of the heterocyclalkylene.

As used herein, the term "aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phen-yl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

As used herein, the term "arylene" refers to an aryl group, as defined above, linking at least two other groups. The two moieties linked to the arylene are linked to different atoms of the arylene. Arylene groups include, but are not limited to, phenylene.

As used herein, the term "arylene-oxy" refers to an arylene group, as defined above, where one of the moieties linked to the arylene is linked through an oxygen atom. Arylene-oxy groups include, but are not limited to, phenylene-oxy.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$-$C_6$)alkyl.

As used herein, the term "alkyl-aryl" refers to a radical having an alkyl component and an aryl component, where the alkyl component links the aryl component to the point of attachment. The alkyl component is as defined above, except that the alkyl component is at least divalent in order to link to the aryl component and to the point of attachment. In some instances, the alkyl component can be absent. The aryl component is as defined above. Examples of alkyl-aryl groups include, but are not limited to, benzyl.

As used herein, the term "alkenyl-aryl" refers to a radical having both an alkenyl component and a aryl component, where the alkenyl component links the aryl component to the point of attachment. The alkenyl component is as defined above, except that the alkenyl component is at least divalent in order to link to the aryl component and to the point of attachment. The aryl component is as defined above. Examples of alkenyl-aryl include ethenyl-phenyl, among others.

As used herein, the term "Heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

As used herein, the term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

As used herein, the term "immune disorder" refers to a dysfunction of the immune system. An immune disorder can be characterized in several ways, including certain components involved in the immune system, whether the immune system is overactive or underactive, or whether the disorder is congenital or acquired. An immune disorder can include an autoimmune disorder including multiple sclerosis, myasthenia gravis, Guillan-Barre syndrome (antiphospholipid syndrome), systemic lupus erytromatosis, Behcet's syndrome, Sjogrens syndrome, rheumatoid arthritis, Hashimoto's disease/hypothyroiditis, primary biliary cirrhosis, mixed connective tissue disease, chronic active hepatitis, Graves' disease/hyperthyroiditis, scleroderma, chronic idiopathic thrombocytopenic purpura, diabetic neuropathy and septic shock. An immune disorder can further include immunodeficiency disorders and allergies.

"Subject" refers to animals such as mammals, including, but not limited to, primates (e.g., humans), cows, sheep, goats, horses, dogs, cats, rabbits, rats, mice and the like. In certain embodiments, the subject is a human.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

As used herein, the term "pharmaceutically acceptable excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

As used herein, the terms "administer" or "administering" refer to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

As used herein, the terms "treat" or "treating" or "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

As used herein, the terms "patient" or "patient in need" refers to a subject suffering from an autoimmune disorder including multiple sclerosis, myasthenia gravis, Guillan-Barre syndrome (antiphospholipid syndrome), systemic lupus erytromatosis, Behcet's syndrome, Sjogrens syndrome, rheumatoid arthritis, Hashimoto's disease/hypothyroiditis, primary biliary cirrhosis, mixed connective tissue disease, chronic active hepatitis, Graves' disease/hyperthyroiditis, scleroderma, chronic idiopathic thrombocytopenic purpura, diabetic neuropathy and septic shock. Patients suffering from other conditions treatable with the disclosed compounds are also treatable with the methods of the present invention. Patients treatable using the methods of the present invention are animals such as mammals, including, but not limited to, primates (e.g., humans), cows, sheep, goats, horses, dogs, cats, rabbits, rats, mice and the like. In certain embodiments, the patient is a human.

III. Compounds

The present invention provides compounds for treating autoimmune disorders.

In some embodiments, the present invention provides compounds of formula Ia:

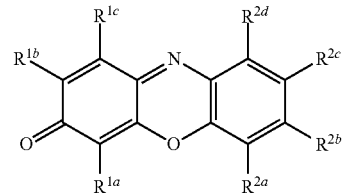

wherein each of $R^{1a}$, $R^{1b}$, and $R^{1c}$ is independently selected from the group consisting of hydrogen, alkyl, substituted alkyl, alkylene, substituted alkylene, heteroalkyl, substituted heteroalkyl, alkoxy, alkenyl, alkenylene, alkynyl, alkynylene, amine, alkyl amine, halogen, haloalkyl, halo-alkoxy, cycloakyl, cycloalkylene, heterocycloalkyl, heterocycloalkylene, aryl, arylene, arylene-oxy, alkyl-aryl, alkenyl-aryl, and heteroaryl, and each of $R^{2a}$, $R^{2b}$, $R^{2c}$, and $R^{2d}$ is independently selected from the group consisting of hydrogen, alkyl, substituted alkyl, alkylene, substituted alkylene, heteroalkyl, substituted heteroalkyl, alkoxy, alkenyl, alkenylene, alkynyl, alkynylene, amine, alkyl amine, halogen, haloalkyl, halo-alkoxy, cycloakyl, cycloalkylene, heterocycloalkyl, heterocycloalkylene, aryl, arylene, arylene-oxy, alkyl-aryl, alkenyl-aryl, and heteroaryl. With the proviso that when $R^{1b}$ is —NH$_2$, then $R^{1c}$ or $R^{2d}$ is not —CO$_2$H.

With the proviso that when $R^{1c}$ and $R^{2d}$ are —$CO_2H$, then $R^{1b}$ is not —$NH_2$. The compounds of formula 1a include salts and isomers thereof.

In some other embodiments, the present invention provides compounds of formula Ib:

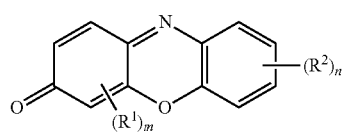

wherein each $R^1$ is independently selected from the group consisting of hydrogen, alkyl, substituted alkyl, alkylene, substituted alkylene, heteroalkyl, substituted heteroalkyl, alkoxy, alkenyl, alkenylene, alkynyl, alkynylene, amine, alkyl amine, halogen, haloalkyl, halo-alkoxy, cycloakyl, cycloalkylene, heterocycloalkyl, heterocycloalkylene, aryl, arylene, arylene-oxy, alkyl-aryl, alkenyl-aryl, and heteroaryl, and each $R^2$ is independently selected from the group consisting of hydrogen, hydrogen, alkyl, substituted alkyl, alkylene, substituted alkylene, heteroalkyl, substituted heteroalkyl, alkoxy, alkenyl, alkenylene, alkynyl, alkynylene, amine, alkyl amine, halogen, haloalkyl, halo-alkoxy, cycloakyl, cycloalkylene, heterocycloalkyl, heterocycloalkylene, aryl, arylene, arylene-oxy, alkyl-aryl, alkenyl-aryl, and heteroaryl. Subscript m of formula 1b is an integer from 1 to 3, and subscript n is an integer from 1 to 4. The compounds of formula 1b include salts and isomers thereof.

In yet some other embodiments, the compound of formula Ib is:

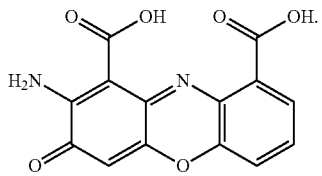 [SMILES: Nc1c(C(=O)O)c2nc3c(C(=O)O)cccc3oc-2cc1=O]

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention can be prepared by a variety of methods known to one of skill in the art, for example, see Richard C. Larock, *Comprehensive Organic Transformations* 1989, VCH Publishers, Inc.

IV. Compositions and Administration

The present invention also provides compositions of a compound of the present invention and a pharmaceutically acceptable excipient. In some embodiments, the compound of the present invention is a compound of formula Ia or Ib. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

The compounds of the present invention can be administered as frequently as necessary, including hourly, daily, weekly or monthly. The compounds utilized in the pharmaceutical method of the invention are administered at the initial dosage of about 0.0001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of disease diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired. Doses can be given daily, or on alternate days, as determined by the treating physician. Doses can also be given on a regular or continuous basis over longer periods of time (weeks, months or years), such as through the use of a subdermal capsule, sachet or depot, or via a patch.

The pharmaceutical compositions can be administered to the patient in a variety of ways, including topically, parenterally, intravenously, intradermally, intramuscularly, colonically, rectally or intraperitoneally. Preferably, the pharmaceutical compositions are administered parenterally, topically, intravenously, intramuscularly or orally.

The compounds of the present invention can be administered to a subject using any suitable methods known in the art. For example, a compound of formula Ia or Ib can be formulated as pharmaceutical compositions with a pharmaceutically acceptable diluent, carrier or excipient. Suitable formulations for use in the present invention are found in Remington's Pharmaceutical Sciences (17th ed. 1985)), which is incorporated herein by reference. A brief review of methods for drug delivery is also described in, e.g., Langer, Science 249:1527-1533 (1990), which is incorporated herein by reference.

A compound of formula Ia or Ib can be administered in any pharmaceutically acceptable composition. A pharmaceutically acceptable nontoxic composition is formed by incorporating any of normally employed excipients, and generally 10-95% of active ingredient and more preferably at a concentration of 25%-75%. Furthermore, to improve oral absorption of a compound of formula Ia or Ib, various carrier systems, such as nanoparticles, microparticles, liposomes, phospholipids, emulsions, erythrocytes, etc. can be used. The oral agents comprising a compound of formula Ia or Ib of the invention can be in any suitable form for oral administration, such as liquid, tablets, capsules, or the like. The oral formulations can be further coated or treated to prevent or reduce dissolution in stomach.

Furthermore, a compound of formula Ia or Ib can be formulated for parenteral, topical, nasal, sublingual, gavage, or local administration. For example, the pharmaceutical compositions are administered parenterally, e.g., intravenously, subcutaneously, intradermally, or intramuscularly, or intranasally. Thus, the invention provides compositions for parenteral administration that comprise a solution of a single or mixture of a compound of formula Ia or Ib, dissolved or suspended in an acceptable carrier, preferably an aqueous carrier. A variety of aqueous carriers may be used including, for example, water, buffered water, 0.4% saline, 0.3% glycine, hyaluronic acid and the like. These compositions may be sterilized by conventional, well known sterilization techniques, or they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

For aerosol administration, a compound of formula Ia or Ib is preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

For solid compositions, conventional nontoxic solid carriers may be used. Solid carriers include, for example, pharmaceutical grades of mannitol, lactose, starch, magnesium stearate, sodium saccharin, talcum, cellulose, glucose, sucrose, magnesium carbonate, and the like.

Compounds of the present invention can also be introduced into an animal cell, preferably a mammalian cell, via a liposomes and liposome derivatives such as immunoliposomes and lipid:nucleic acid complexes. The term "liposome" refers to vesicles comprised of one or more concentrically ordered lipid bilayers, which encapsulate an aqueous phase. The aqueous phase typically contains the compound to be delivered to the cell, i.e., a compound of formula 1a and 1b.

The liposome fuses with the plasma membrane, thereby releasing the a compound of formula 1a or 1b into the cytosol. Alternatively, the liposome is phagocytosed or taken up by the cell in a transport vesicle. Once in the endosome or phagosome, the liposome either degrades or fuses with the membrane of the transport vesicle and releases its contents.

In current methods of drug delivery via liposomes, the liposome ultimately becomes permeable and releases the encapsulated compound (in this case, a compound of formula Ia or Ib) at the target tissue or cell. For systemic or tissue specific delivery, this can be accomplished, for example, in a passive manner wherein the liposome bilayer degrades over time through the action of various agents in the body. Alternatively, active drug release involves using an agent to induce a permeability change in the liposome vesicle. Liposome membranes can be constructed so that they become destabilized when the environment becomes acidic near the liposome membrane (see, e.g., Proc. Nat'l Acad. Sci. USA 84:7851 (1987); Biochemistry 28:908 (1989)). When liposomes are endocytosed by a target cell, for example, they become destabilized and release their contents. This destabilization is termed fusogenesis. Dioleoylphosphatidylethanolamine (DOPE) is the basis of many "fusogenic" systems.

Such liposomes typically comprise a compound of formula Ia or Ib and a lipid component, e.g., a neutral and/or cationic lipid, optionally including a receptor-recognition molecule such as an antibody that binds to a predetermined cell surface receptor or ligand (e.g., an antigen). A variety of methods are available for preparing liposomes as described in, e.g., Szoka et al., Ann. Rev. Biophys. Bioeng. 9:467 (1980), U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91/17424, Deamer & Bangham, Biochim. Biophys. Acta 443:629-634 (1976); Fraley, et al., Proc. Nat'l Acad. Sci. USA 76:3348-3352 (1979); Hope ct al., Biochim. Biophys. Acta 812:55-65 (1985); Mayer et al., Biochim. Biophys. Acta 858:161-168 (1986); Williams et al., Proc. Nat'l Acad. Sci. USA 85:242-246 (1988); Liposomes (Ostro (ed.), 1983, Chapter 1); Hope et al., Chem. Phys. Lip. 40:89 (1986); Gregoriadis, Liposome Technology (1984) and Lasic, Liposomes: from Physics to Applications (1993)). Suitable methods include, for example, sonication, extrusion, high pressure/homogenization, microfluidization, detergent dialysis, calcium-induced fusion of small liposome vesicles and ether-fusion methods, all of which are well known in the art.

In certain embodiments of the present invention, it is desirable to target the liposomes of the invention using targeting moieties that are specific to a particular cell type, tissue, and the like. Targeting of liposomes using a variety of targeting moieties (e.g., ligands, receptors, and monoclonal antibodies) has been previously described (see, e.g., U.S. Pat. Nos. 4,957,773 and 4,603,044). Standard methods for coupling targeting agents to liposomes can be used. These methods generally involve incorporation into liposomes lipid components, e.g., phosphatidylethanolamine, which can be activated for attachment of targeting agents, or derivatized lipophilic compounds, such as lipid derivatized bleomycin. Antibody targeted liposomes can be constructed using, for instance, liposomes which incorporate protein A (see Renneisen et al., J. Biol. Chem., 265:16337-16342 (1990) and Leonetti et al., Proc. Nat'l Acad. Sci. USA 87:2448-2451 (1990).

In some therapeutic applications, a compound of formula 1a or 1b of the invention is administered to a patient in an amount sufficient to decrease symptoms of an autoimmune disorder. An amount adequate to accomplish this is defined as "therapeutically effective dose." Amounts effective for this use will depend on, for example, the particular compound of formula Ia or Ib employed, the manner of administration, the weight and general state of health of the patient, and the judgment of the prescribing physician. "Therapeutically effective dose" also encompasses doses that are sufficient to prevent an autoimmune disease from developing in a subject. Thus, prophylactic doses are encompassed by the term "therapeutically effective dose." The foregoing are general guidelines only that can be expanded or altered based on, for example, disease type and grade, patient age, health status, and sex, the particular drugs used in combination, the route and frequency of administration, and experimental and clinical findings using a multidrug combination.

V. Methods of Treating Immune Disorders

In some embodiments, the present invention provides methods for preventing and treating an autoimmune disorder in a subject. The method comprises administering to the subject a compound of formula 1a or 1b in an amount sufficient prevent or treat an autoimmune disorder such as multiple sclerosis, myasthenia gravis, Guillan-Barre syndrome (antiphospholipid syndrome), systemic lupus crytromatosis, Behcet's syndrome, Sjogrens syndrome, rheumatoid arthritis, Hashimoto's disease/hypothyroiditis, primary biliary cirrhosis, mixed connective tissue disease, chronic active hepatitis, Graves' disease/hyperthyroiditis, scleroderma, chronic idiopathic thrombocytopenic purpura, diabetic neuropathy and septic shock.

In another aspect, the present invention provides a method of modulating Aryl Hydrocarbon Receptor (AHR) activity for treating and/or preventing autoimmune disorders. In some embodiments the method includes contacting a compound of formula 1a or 1b with the AHR. In some embodiments the method includes contacting a compound of formula Ia or Ib or a pharmaceutical composition thereof, with the AHR.

Treatment methods provided herein include, in general, administration to a patient an effective amount of one or more compounds provided herein, e.g., orally, nasally or parenterally. Suitable patients include those patients suffering from or susceptible to (i.e., prophylactic treatment) a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient an effective amount of a compound of formula 1a or 1b. In one embodiment, the compound(s) of the invention are administered to a patient (e.g., a human) orally. The effective amount may be an amount sufficient to modulate the AHR receptor and/or an amount sufficient to reduce or alleviate the symptoms presented by the patient. Treatment regimens may vary depending on the compound used and the particular condition to be treated. The compounds of the present invention can be administered as frequently as necessary, including hourly, daily, weekly or monthly. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired. Doses can be given daily, or on alternate days, as determined by the treating physician. Doses can also be given on a regular or continuous basis over longer periods of time (weeks, months or years), such as through the use of a subdermal capsule, sachet or depot, or via a patch.

The pharmaceutical compositions can be administered to the patient in a variety of ways, including topically, parenterally, intravenously, intradermally, intramuscularly, colonically, rectally or intraperitoneally. Preferably, the pharmaceutical compositions are administered parenterally, topically, intravenously, intramuscularly or orally.

VI. Examples

The following examples are offered to illustrate, but not to limit the claimed invention.

Example 1

FIG. 1 shows that Cinnabarinic Acid inhibits the development of experimental allergic encephalomyelitis (EAE) in C57BL/6 mice with a single dose given at the time that MOG peptide and CFA were injected—Day 0

Example 2

Figure 2:
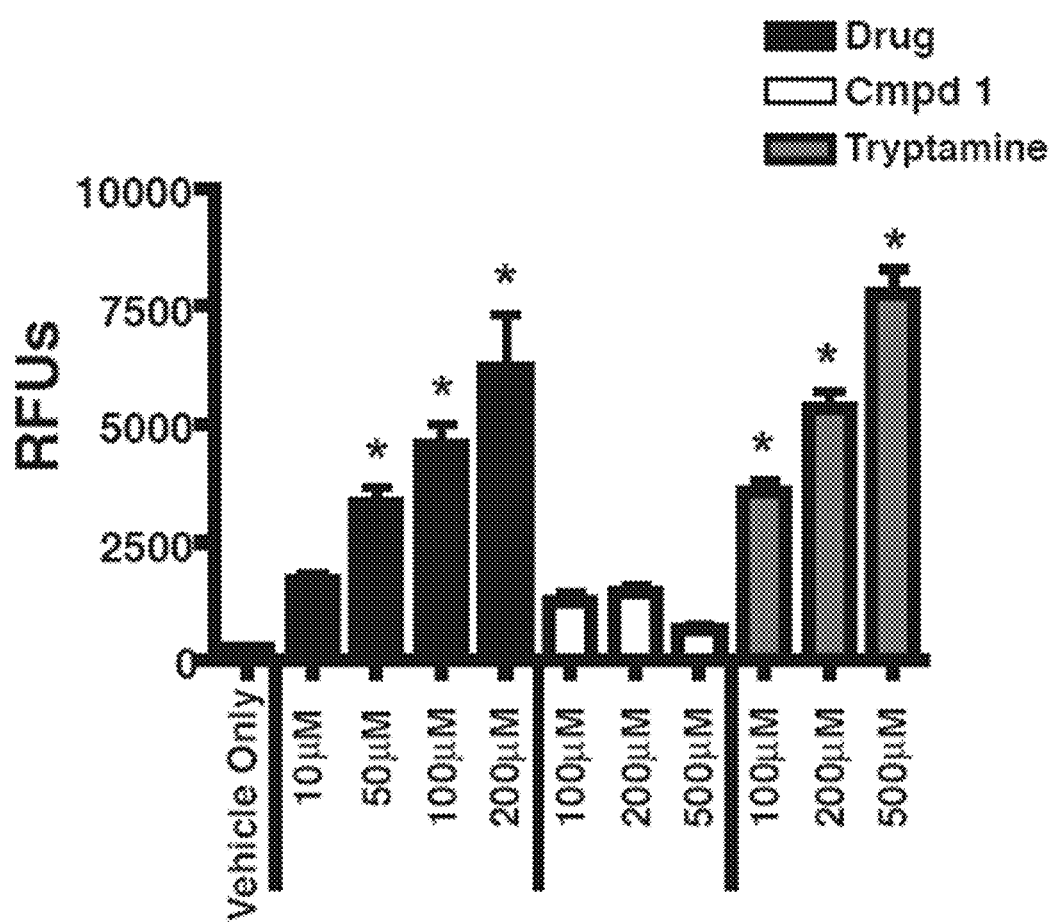
FIG. 2 illustrates that Cinnabarinic Acid activates AHR responsive (Dioxin Responsive Elements) in an in vitro test demonstrating agonist activity. Tryptamine is a positive control and a downstream related molecule (Compound 1) is a negative control.

FIG. 2 shows that Cinnabarinic Acid activates AHR responsive (Dioxin Responsive Elements) in an in vitro test demonstrating agonist activity. Tryptamine is a positive control and a downstream related molecule (Compound 1) is a negative control

Example 3

Figure 3:
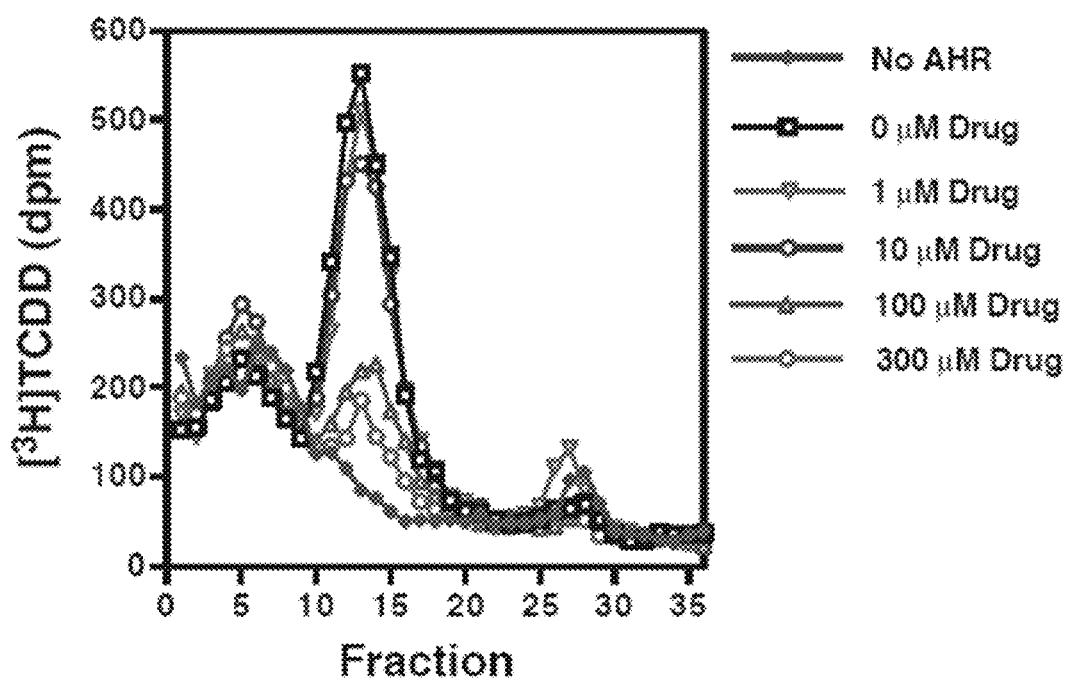
FIG. 3 illustrates that Cinnabarinic Acid displaces Dioxin (TCDD) in an in vitro assay using purified in vitro translated human AHR protein thereby demonstrating direct binding.

FIG. 3 shows that Cinnabarinic Acid displaces Dioxin (TCDD) in an in vitro assay using purified in vitro translated human AHR protein thereby demonstrating direct binding

Example 4

Figure 4:
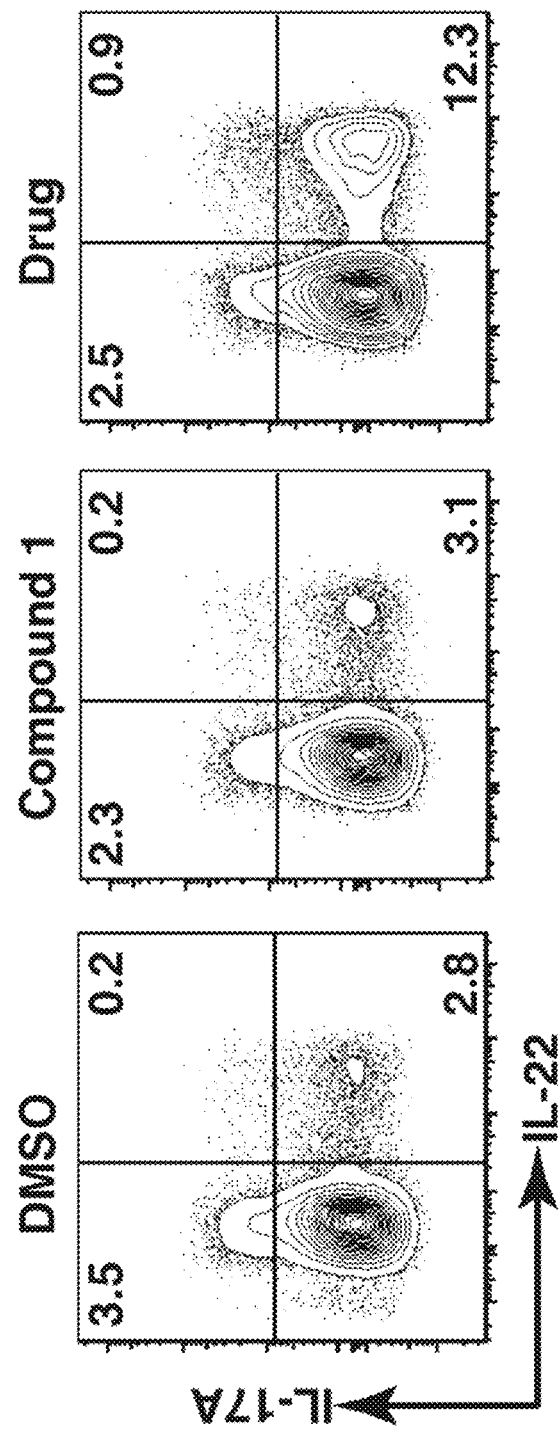
FIG. 4 illustrates that Cinnabarinic Acid potently induces IL-22 in vitro in cultured human naïve CD4+ T cells stimulated with anti-CD3/anti-CD28 under "Th17" polarizing conditions (IL-1b, IL-21, IL-23 with anti-IFNg and anti-IL4). This is AHR dependent as inclusion of an AHR antagonist fully abrogated effect.

FIG. 4 shows that Cinnabarinic Acid potently induces IL-22 in vitro in cultured human naïve CD4+ T cells stimulated with anti-CD3/anti-CD28 under "Th17" polarizing conditions (IL-1b, IL-21, IL-23 with anti-IFNg and anti-IL4). This is AHR dependent as inclusion of an AHR antagonist fully abrogated effect.

Example 5

Figure 5:
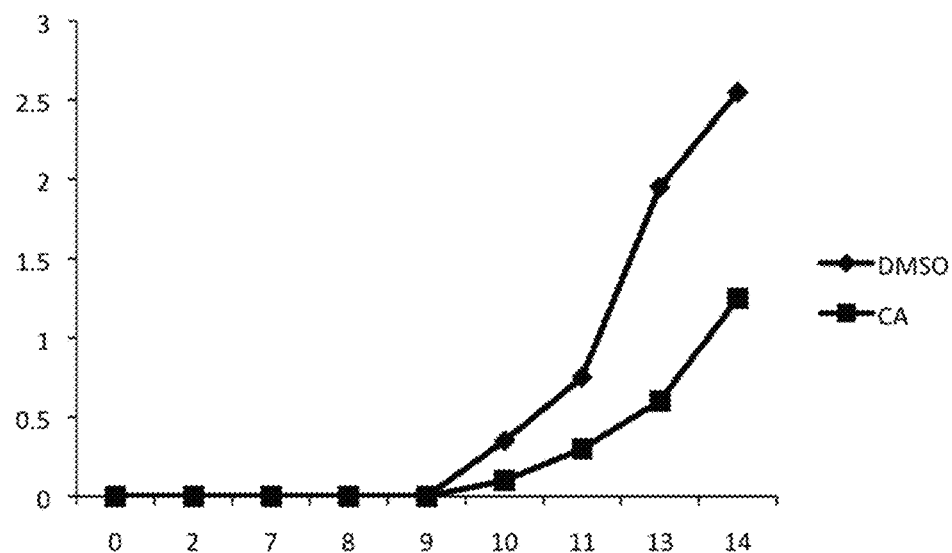
FIG. 5 illustrates that Cinnabarinic Acid inhibits the induction of EAE as compared to DMSO.
Figure 5:
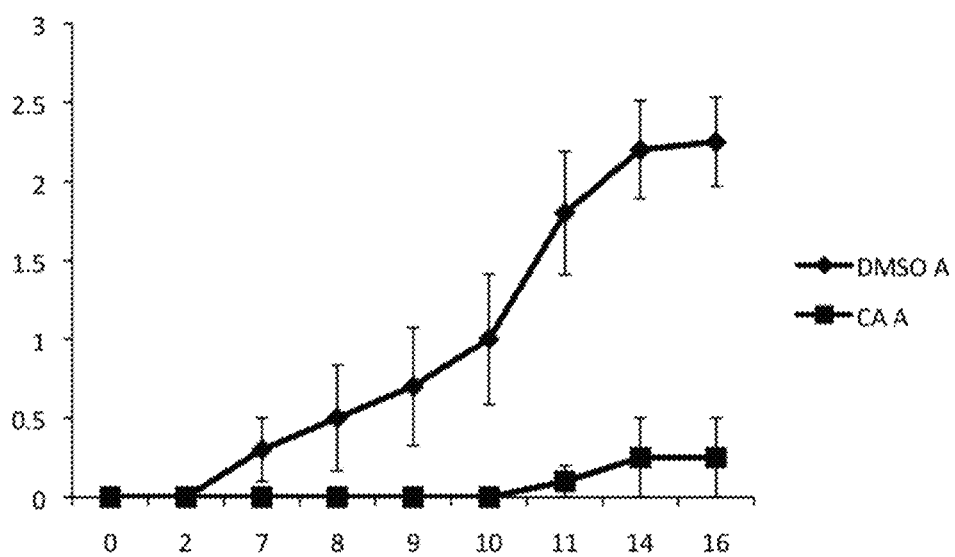

FIG. 5 shows that Cinnabaric Acid inhibits the induction of EAE as compared to DMSO.

Example 6

The aryl hydrocarbon receptor (AHR) binds to environmental toxins and synthetic aromatic halogenated hydrocarbons and is involved in a diverse array of biological processes. Recently the AHR was shown to control host immunity by affecting the balance between inflammatory T cells that produce interleukin 17 (Th17) and regulatory T cells (Treg) that are involved in tolerance. While environmental toxins were shown to mediate this effect, suggesting a link between pollutants and autoimmunity, it is likely that natural ligands also exist which may play an important role in regulating host immune responses in a similar manner. We investigated downstream metabolites of tryptophan as potential AHR ligands because (1) tryptophan metabolites have been implicated in regulating the balance between Th17 and Treg cells and (2) many of the AHR ligands identified thus far are derivatives of tryptophan. Here we identify cinnabarinic acid (CA) as an AHR ligand downstream of inflammatory tryptophan metabolism. CA was found to stimulate the differentiation of a newly defined subset of human T cells that produce the cytokine IL-22, but not IL-17, and suppress autoimmunity in a mouse model of multiple sclerosis. Our findings link inflammatory tryptophan metabolism to activation of the AHR in humans and mice and define a novel endogenous ligand of the AHR that may have broad biological functions.

The enzyme indole 2,3-dioxygenase (IDO) plays an important role in the regulation of both the innate and adaptive immune system in settings such as cancer, autoimmunity, microbial pathogenesis, and pregnancy (1-4). IDO is the first, rate-limiting step in the metabolism of the essential amino acid tryptophan to kynurenine and is induced under certain inflammatory conditions, most notably in response to interferons (IFN) (reviewed in 5). Two non-exclusive mechanisms have been suggested for how IDO affects immunity: (a) through depleting local tryptophan levels leading to the induction of the 'amino acid starvation' response (6), and (b) through the generation of kynurenine and other downstream metabolites which have specific immunomodulatory or cytotoxic functions (7). Tryptophan metabolites generated through the IDO pathway have been shown to suppress T cell activation and to affect T cell differentiation pathways, although the means by which they achieve these effects remain largely unknown (8-10). A potential mechanism that was recently identified suggests that tryptophan metabolites can alter the balance of Treg cells and Th17 cells, two related populations of T cells that have opposing functions during immune responses (11).

Treg and Th17 cells share similar developmental pathways and may arise from a common progenitor population (12). Several different mechanisms have been identified that govern the decision of a T cell to become a Treg or Th17 cell including the presence of inflammatory cytokines (IL-1b, IL-6, IL-21, IL-23) (13), retinoic acid (14), and activation of the AHR (15,16). The AHR is a cytosolic transcription factor that is involved in many biological processes including development, cellular differentiation and proliferation, metabolism of xenobiotic agents, and the immune response (reviewed in 15). The best-studied ligands to date are synthetic halogenated and polycyclic aromatic hydrocarbons (most notably 2,3,7,8-tetrachlorodibenzodioxin, (TCDD)) (17). Only a few natural endogenous ligands have been identified, many of which are tryptophan derivatives. These include 2-(1'H-indole-3'-carbonyl)-thiazole-4-carboxylic acid methyl ester (ITE), tryptamine, indigo and indirubin, and 6-formylindolo[3,2-b]carbazole (FICZ) (17). The highly conserved nature of the AHR signaling pathway has prompted the search for additional endogenous ligands that can be directly linked to physiological functions. We therefore sought to determine whether tryptophan metabolites downstream of IDO might act as AHR ligands.

Figure 6:
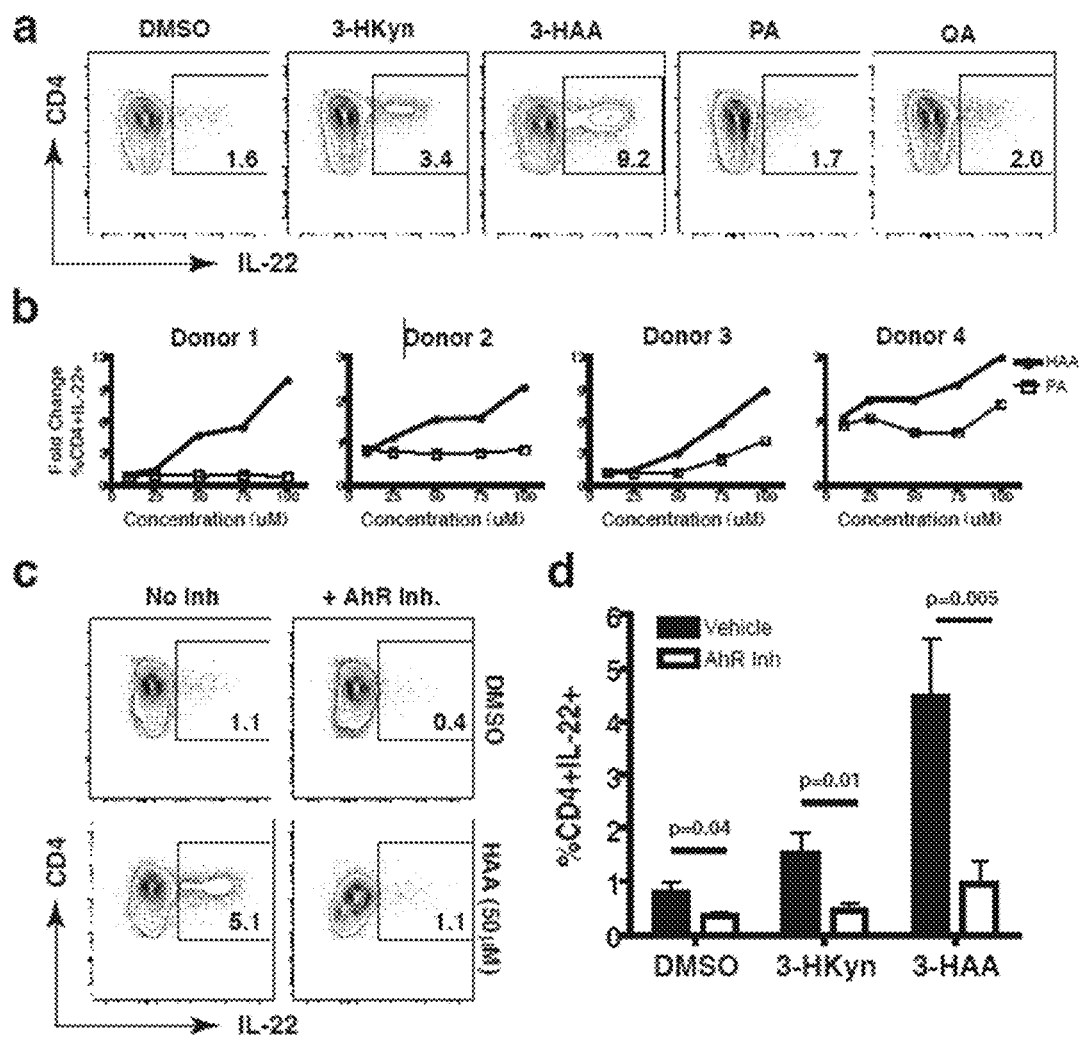
FIG. 6: 3-HKyn and 3-HAA promote IL-22 expression by stimulated human CD4+ T cells. (A) Stimulation of human PBMCs in the presence of 100 μM 3-HKyn and 100 μM 3-HAA, but not the downstream metabolites PA or QA, leads to the expansion of a population of cells expression the cytokine IL-22. (B) 3-HAA promotes IL-22 expression in dose-dependent manner but to a variable extent between individual donors. (C) IL-22 induction by 3-HAA is blocked by inhibition of the AhR pathway. (D) Summary of 3 different experiments with 6 donors demonstrating that inhibition of the AhR blocks IL-22 upregulation by 3-HAA.

3-Hydroxyanthranilic Acid (3-HAA) Induces IL-22 Expression by Activated CD4+ T Cells Although the AHR was initially proposed to impact Treg and Th17 development, more recent findings suggest that the expression of the cytokine IL-22, which is often co-expressed by Th17 cells in mice, is more greatly impacted by AHR activation (16). This is highlighted by the observation that AHR−/− mice retain the ability to generate some Th17 cells, but are incapable of generating cells that express IL-22 (16-18). Human T cells were also found to exhibit distinct requirements for the AHR in T cell differentiation. Activation of the AHR in stimulated human T cells by FICZ was found to have inhibitory effects, if any, on Th17 differentiation, but promoted a significant increase in the frequency of CD4+ T cells that produced IL-22 (Th22) (19). To screen for the ability of tryptophan metabolites generated downstream of IDO to activate the AHR, we stimulated human T cells in vitro in the presence of different tryptophan metabolites (3-Hydroxykynurenine (3-HKA), 3-Hydroxyanthranilic Acid (3-HAA), Picolinic Acid (PA), and Quinolinic Acid (QA)) to assess whether any promoted the expansion of CD4+ T cells secreting IL-22. We found that 3-HKA and 3-HAA, but not the downstream metabolites PA or QA, were able to promote the differentiation of Th22 cells (FIG. 6A). These cells frequently co-expressed IFNγ but were generally found to be IL-17A negative, suggesting a phenotype comparable to the Th22 cells recently identified in humans (19). We also found that different donors induced different levels of IL-22 upon activation although in each case 3-HAA was able to promote at least a 2-fold expansion of Th22 cells (FIG. 6B). To determine whether the induction of IL-22 within this population was dependent upon AHR activation, we next stimulated human T cells in the presence or absence of a potent AHR antagonist (CH-223191) and monitored the induction of IL-22. We observed that CH-223191 was able to significantly abolish IL-22 induction by 3-HAA, suggesting that the AHR was required for this effect (FIG. 6C, D).

3-HKA and 3-HAA are not AHR Ligands but May be Precursors to an AHR Ligand

Our initial screen examining AHR-dependent induction of IL-22 by human CD4+ T cells indicated that 3-HAA, and to a lesser extent 3-HKA, were potential ligands of the AHR. Because 3-HKA is a precursor to 3-HAA, we hypothesized that the ability of 3-HKA to promote IL-22 induction resulted from the generation of 3-HAA in our culture conditions, and that 3-HAA was the most likely candidate as an AHR ligand. We performed a precursory screen of all tryptophan metabolites including both 3-HKA and 3-HAA to bind to and act as agonists or antagonists of the AHR using two separate assays. First we examined the ability of 3-HKyn, 3-HAA, and PA to displace TCDD binding to the human AHR protein in vitro (20). We were able to detect modest binding of 3-HAA only at very high concentrations, and were unable to measure any significant displacement using any of the other tryptophan metabolites tested. We also measured AHR activation using a mouse hepatoma cell line (H1G1) that stably expresses a green fluorescent protein (GFP) reporter construct downstream of a series of dioxin responsive elements (FIG. 7A) (21). We measured both agonistic, and antagonistic, activity of each metabolite in addition to known agonists (Tryptamine, FICZ) and antagonists (CH-223191). While we noted a modest increase in AHR activity using 3-HAA as an agonist, this failed to reach significance, and none of the other metabolites (3-HKyn, PA, QA) were found to have any activity as agonists or antagonists. These results suggested that 3-HAA might be an upstream precursor of an AHR ligand.

Figure 7:
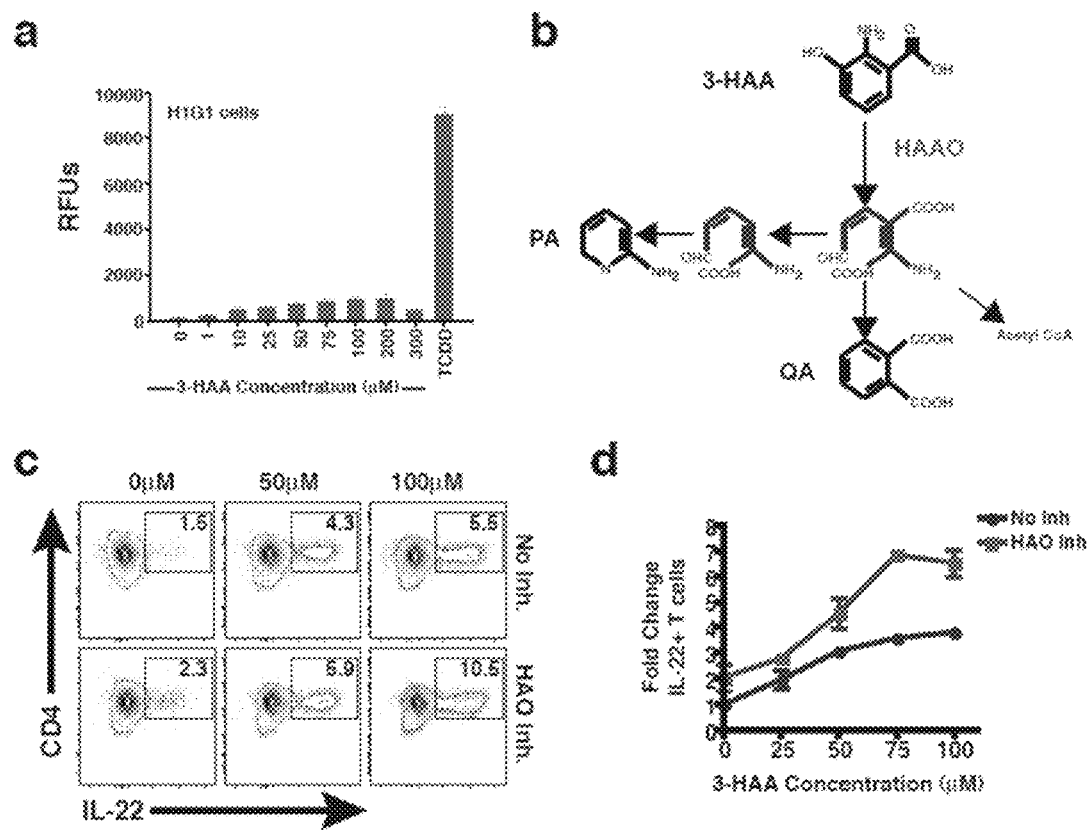
FIG. 7: 3-HAA is not an AhR ligand. (A) Incubation of a murine hepatoma cell line stably transfected with an AhR-responsive (AhR-eGFP) reporter construct in the presence of increasing concentrations of 3-HAA leads to minimal activation of the AhR. (B) Metabolic pathways downstream of 3-HAA catalyzed by the enzyme 3-Hydroxyanthranilate 3,4-Dioxygenase (HAAO) including intermediates upstream of PA and QA generation. (C) HAAO blockade enhances the ability of 3-HAA to promote IL-22 expression by stimulated CD4+ T cells. (D) Summary of two individuals showing that HAAO inhibition increases the ability of 3-HAA to promote IL-22 expression by CD4+ T cells in a dose-dependent manner.

PA and QA are generally regarded as the primary metabolites generated downstream of 3-HAA during tryptophan metabolism through the IDO pathway. As neither of these was found to have any impact on IL-22 induction in our initial screen, we thought it would be unlikely that either was an AHR ligand. The enzyme involved upstream of the generation of PA and QA is called 3-Hydroxyanthranilate 3,4-Dioxygenase (HAAO) and is expressed by the same cell populations that express IDO under inflammatory conditions (22). HAAO converts 3-HAA to 2-amino-3-carboxymuconic semialdehyde, which may be non-enzymatically cyclized to form QA or can be enzymatically converted into 2-amino-muconic-semialdehyde, which in turn cyclizes to form PA (23). 2-amino-3-carboxymuconic semialdehyde can also be further metabolized to form Acetyl-CoA (FIG. 7B) (23). To address whether any downstream intermediates of 3-HAA generated through the activity of the enzyme HAAO were acting as AHR ligands, we utilized the specific HAAO inhibitor 4-fluoro-3-hydroxythranilic acid (4-F-3-HAA), in the presence of different concentrations of 3-HAA, to prevent the generation of downstream metabolites. Surprisingly we observed a stark increase in the ability of 3-HAA to induce IL-22 under our culture conditions (FIG. 7C, D). This finding suggests that alternative pathways are likely to exist which might be involved in the generation of AHR ligands downstream of 3-HAA.

Identification of Cinnabarinic Acid as an AHR Ligand Downstream of 3-HAA

Figure 8:
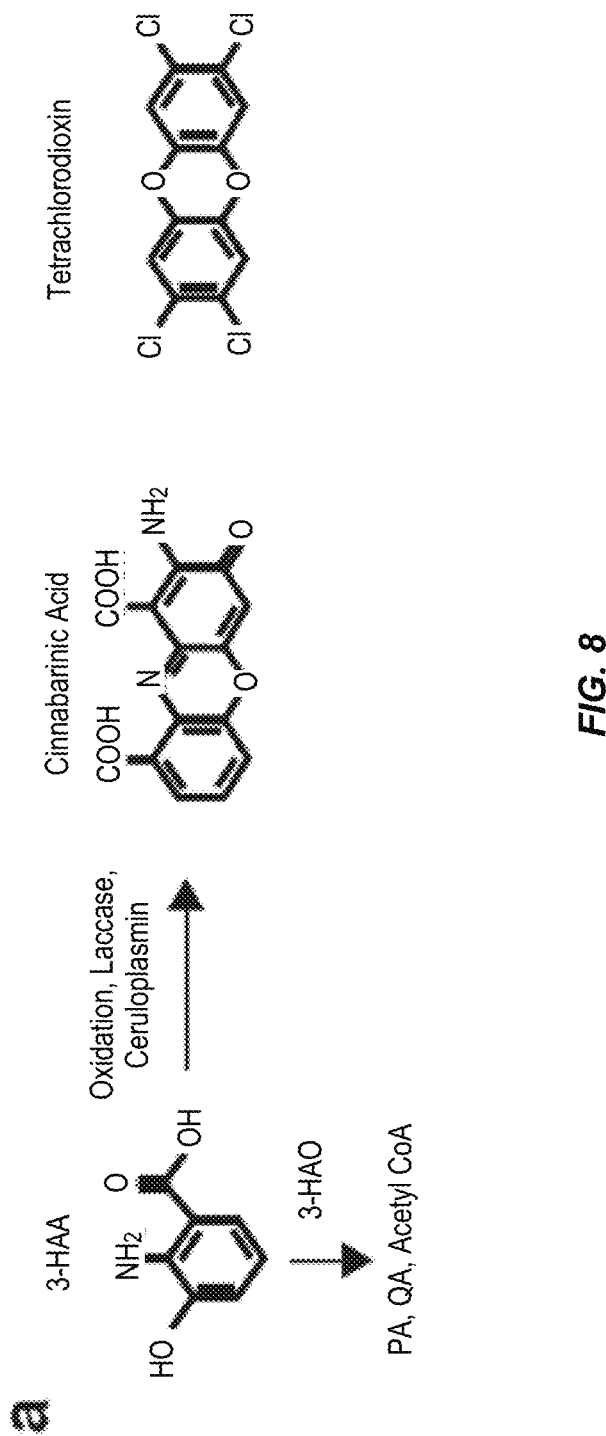
FIG. 8: CA is an endogenous AhR agonist generated by oxidative dimerization of 3-HAA. (A) An alternative pathway of 3-HAA metabolism leads to the generation of CA either by non-enzymatic (oxidation) or enzymatic (laccase, ceruloplasmin) processes. CA is structurally similar to the synthetic AhR ligand TCDD. (B) CA acts as a potent agonist of the AhR, whereas 3-HAA has no activity in short-term assays. Tryptamine is a positive control. (C) Incubation of CA with in vitro translated human AhR protein results in a dose-dependent inhibition of TCDD binding. (D) Incubation of sorted naïve human CD4+ T cells with CA (25 µM) potently induces IL-22 whereas similar concentrations of 3-HAA only had minimal effects. Data are representative of three similar experiments.
Figure 8:
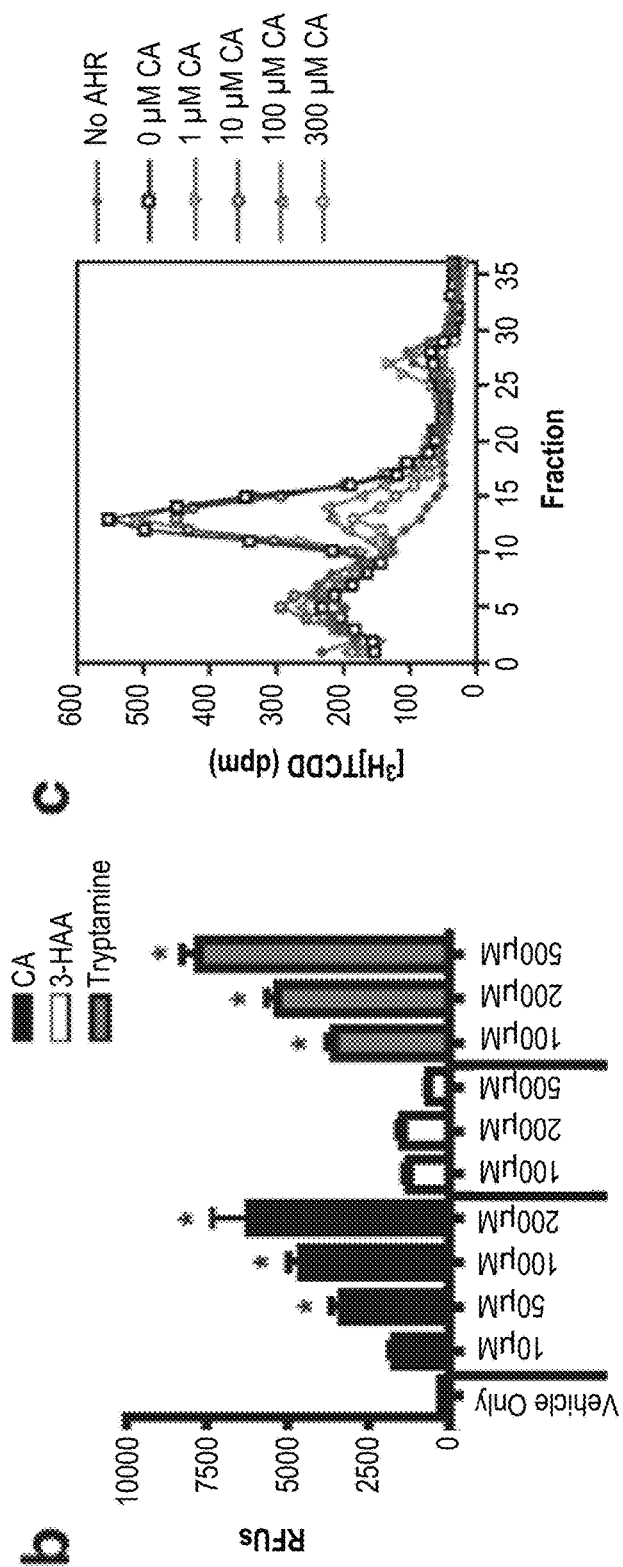
Figure 8:
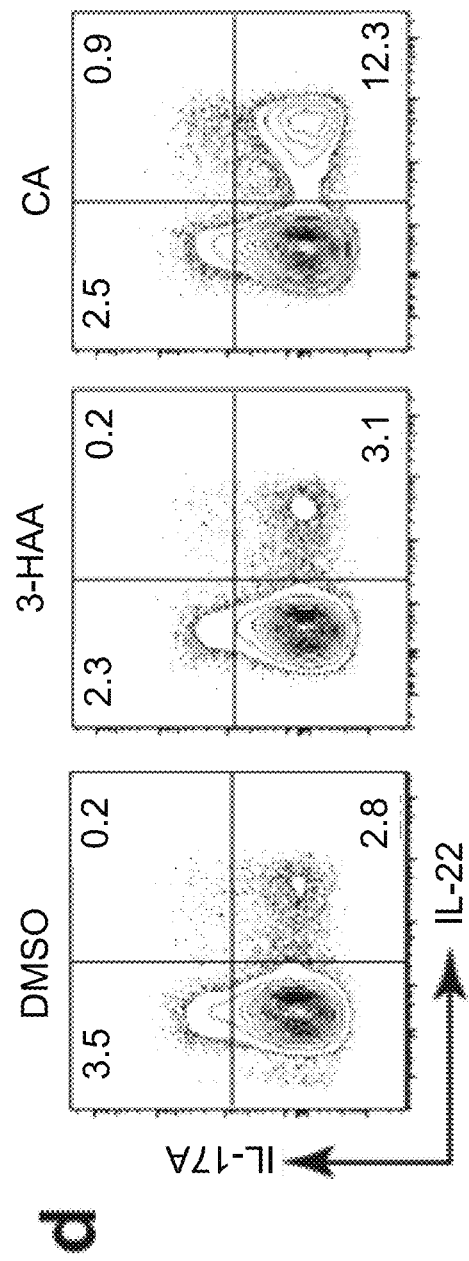

3-HAA is particularly susceptible to oxidation, resulting in the formation of the metabolite cinnabarinic acid (CA) through dimerization of two molecules of 3-HAA (24). As a polycyclic aromatic hydrocarbon, cinnabarinic acid's structural features suggest it may act as an AHR ligand (FIG. 8A). In addition, CA has potent effects on thymocyte maturation (25) not unlike what has been observed in rodents treated with TCDD (26-28) or in transgenic mice with a constitutively active AHR (29). To test the hypothesis that CA is an AHR ligand, we obtained pure CA, prepared through a chemical synthesis using 3-HAA as a starting material and purified by HPLC, and analyzed its ability to bind to and activate the AHR in vitro. We found that CA was able to bind to and activate the AHR at much lower concentrations than that observed for 3-HAA (FIG. 8B), resulting in upregulation of CYP1A1 transcription within lymphocytes. The ability of CA to serve as an AHR ligand is conserved across species, as measured by CA's potent induction of CYP1A1 in zebrafish embryos within 72 hours. Consequently, treatment of activated human naïve CD4+ T cells with CA promoted IL-22 production more strongly than any other tryptophan metabolite tested (FIG. 8C).

The 3-HAA Synthetic Analogue Tranilast is an Antagonist of the AHR

Figure 9:
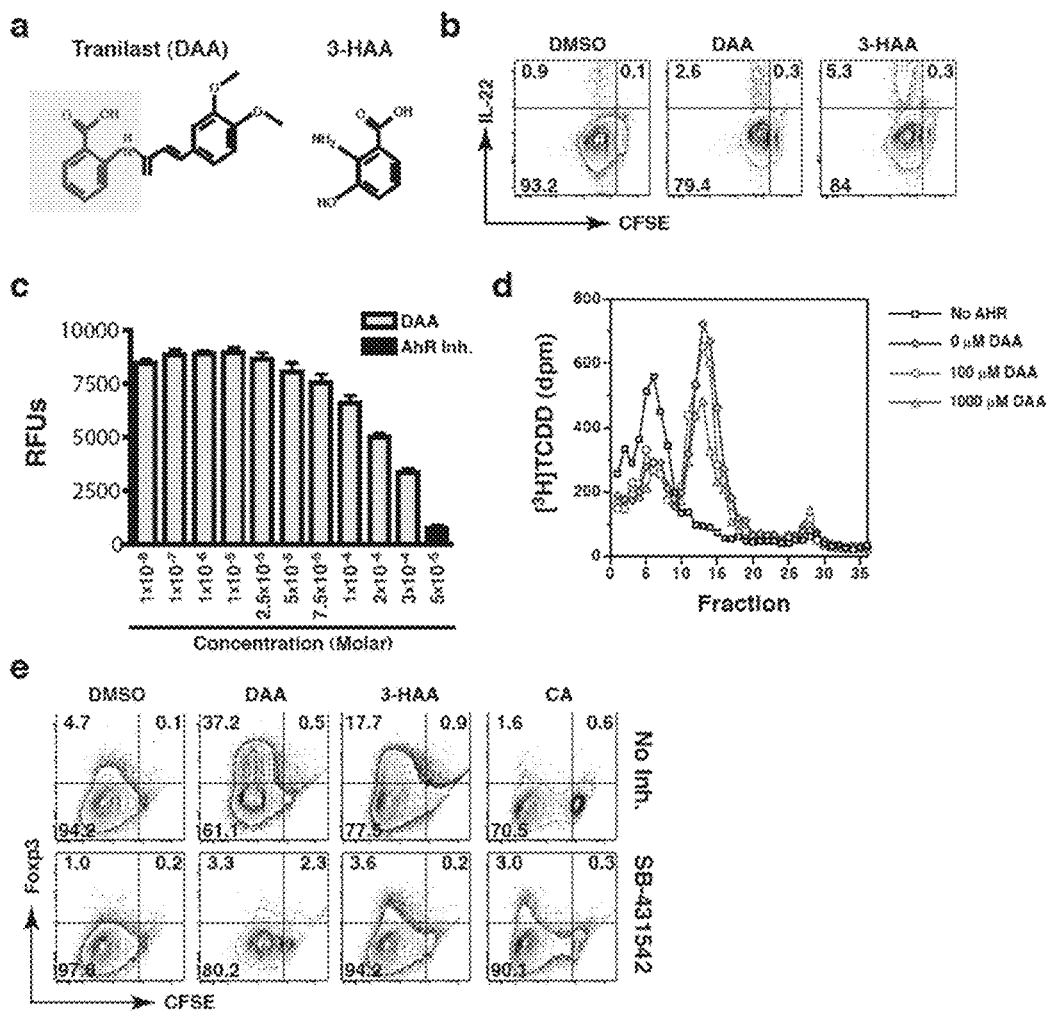
FIG. 9: The synthetic 3-HAA analogue 3,4 DAA (Tranilast) is an AhR antagonist and promotes the induction of Foxp3 by stimulated CD4+ T cells. (A) 3,4 DAA shares some structural similarities to 3-HAA (highlighted region). (B) Stimulation of human PBMCs in the presence of 3,4 DAA induces IL-22 expression by CD4+ T cells but to a lesser extent than 3-HAA. (C) 3,4 DAA inhibits TCDD binding to human AhR in vitro but only at high concentrations (1000 µM). (D) 3,4 DAA is blocks activation of the AhR by TCDD in H1G1 cells suggesting that it is an AhR antagonist. CH223191 (50 mM) is shown as a positive control. (E) 3,4 DAA induces Foxp3 expression in stimulated naïve (CD45RA+CCR7+CD95−CD25−) CD4+ T cells. 3-HAA also promotes Foxp3 upregulation but to a lesser extent. The TGFβ signaling inhibitor SB-431542 (Activin-like kinase1 inhibitor) reversed the ability of 3,4 DAA and 3-HAA to upregulate Foxp3, demonstrating that TGFβ is required for Foxp3 induction.

N-(3,4-dimethoxycinnamonyl) anthranilic acid (3,4-DAA; Tranilast) is thought to have immunosuppressive properties similar to 3-HAA, yet its precise mode of action in suppressing immune responses remains unclear (25). 3,4 DAA shares the anthranilate core with 3-HAA, yet based on its structure, it is unlikely to dimerize into a polycyclic ring system such as that of CA (FIG. 9A). We found that 3,4 DAA promoted a slight increase in the frequency of CD4+ T cells secreting IL-22 in our in vitro stimulations with human T cells (FIG. 9B); in contrast to 3-HAA, 3,4 DAA also dramatically suppressed T cell proliferation in the range of concentrations that were tested. 3,4 DAA was able to bind to the human AHR in vitro in our cell-free system and displace TCDD at relatively high concentrations, similar to those seen for 3-HAA (FIG. 9C), and it had no activity as an AHR agonist in our reporter assays. Co-treatment of our H1G1AHR reporter cells with 3,4 DAA prevented AHR activation by TCDD, indicating 3,4 DAA actually may serve as an AHR antagonist (*NB we could say antagonist of AHR transcriptional activities . . . ), albeit to a lesser extent than the potent antagonist CH-223191 (FIG. 9D).

In a previous report where 3,4 DAA was used to suppress the development of EAE, it was noted that T cells from treated mice were able to suppress EAE upon transfer into wild-type mice, suggesting that the mechanism underlying suppression involved the development of suppressive T cell subsets (25). Therefore we asked whether T cells treated with 3,4 DAA might be prompted to differentiate into Treg cells through upregulation of the transcription factor Foxp3 (26). In accordance with this hypothesis we found that 3,4 DAA promoted a dose-dependent increase in the frequency of CD4+Foxp3+ T cells after stimulation of naïve CD4+ T cells in vitro (FIG. 9E). This effect was enhanced in the presence of increasing concentrations of 3,4 DAA even though proliferation of the T cells was significantly inhibited. By contrast, CA did not appear to promote Foxp3 upregulation in any of the experiments performed (FIG. 9E).

CA Suppresses the Development of Autoimmunity In Vivo

Figure 10A:
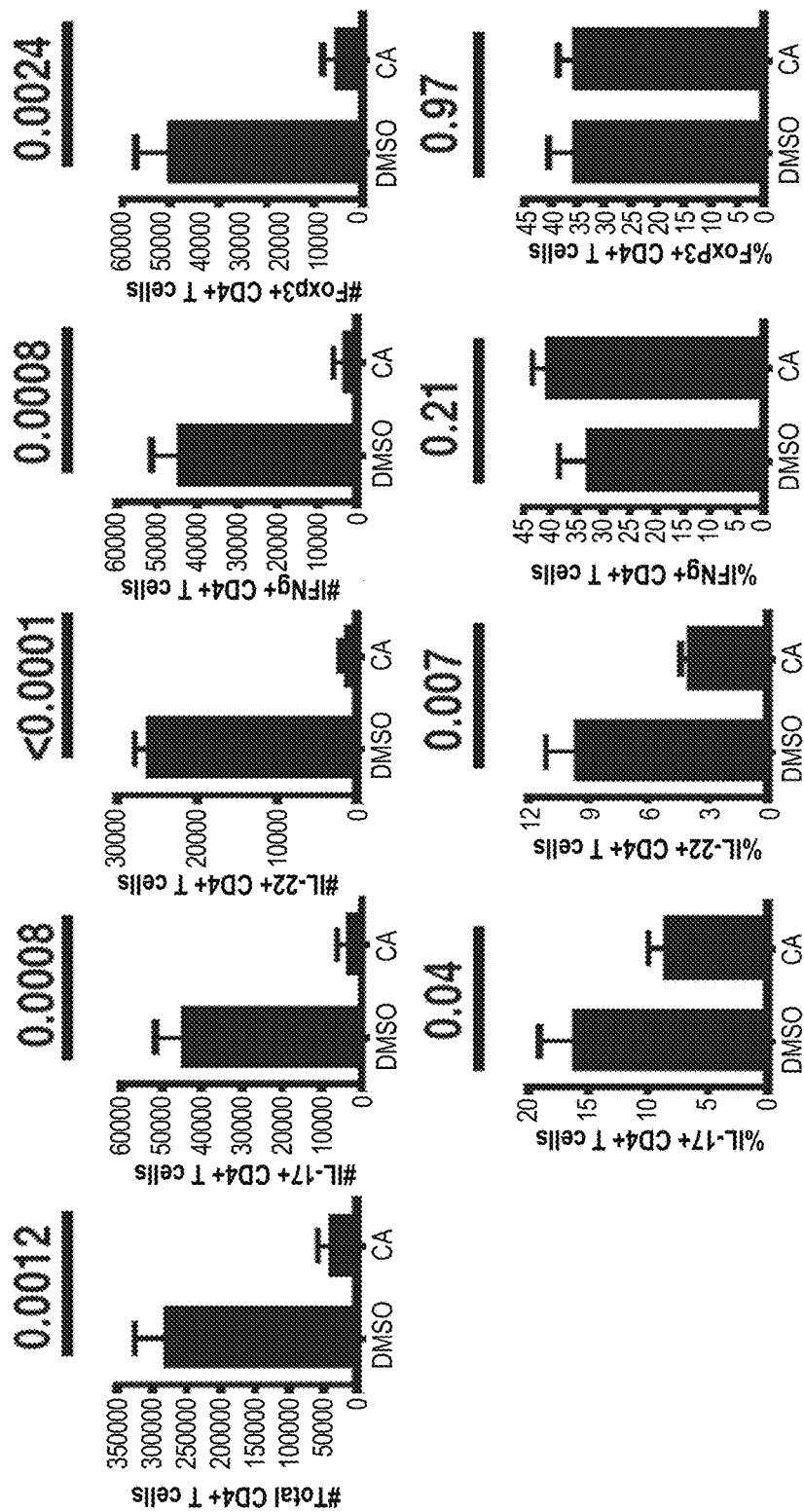
FIGS. 10A and 10B illustrate the number or frequency of cytokine producing cells within the CNS (or spleen) of mice treated at day 0 with 1 dose of CA (1 mg/mouse) or vehicle (DMSO) within the emulsion contain MOG peptide and adjuvant. Representative flow plots are shown at the bottom of the figures. EAE survival curve for 10 animals treated with CA or with DMSO showing that 1/10 animals treated with CA gets sick whereas 9/10 animals treated with vehicle (DMSO) are sick at the indicated timepoint.
Figure 10A:
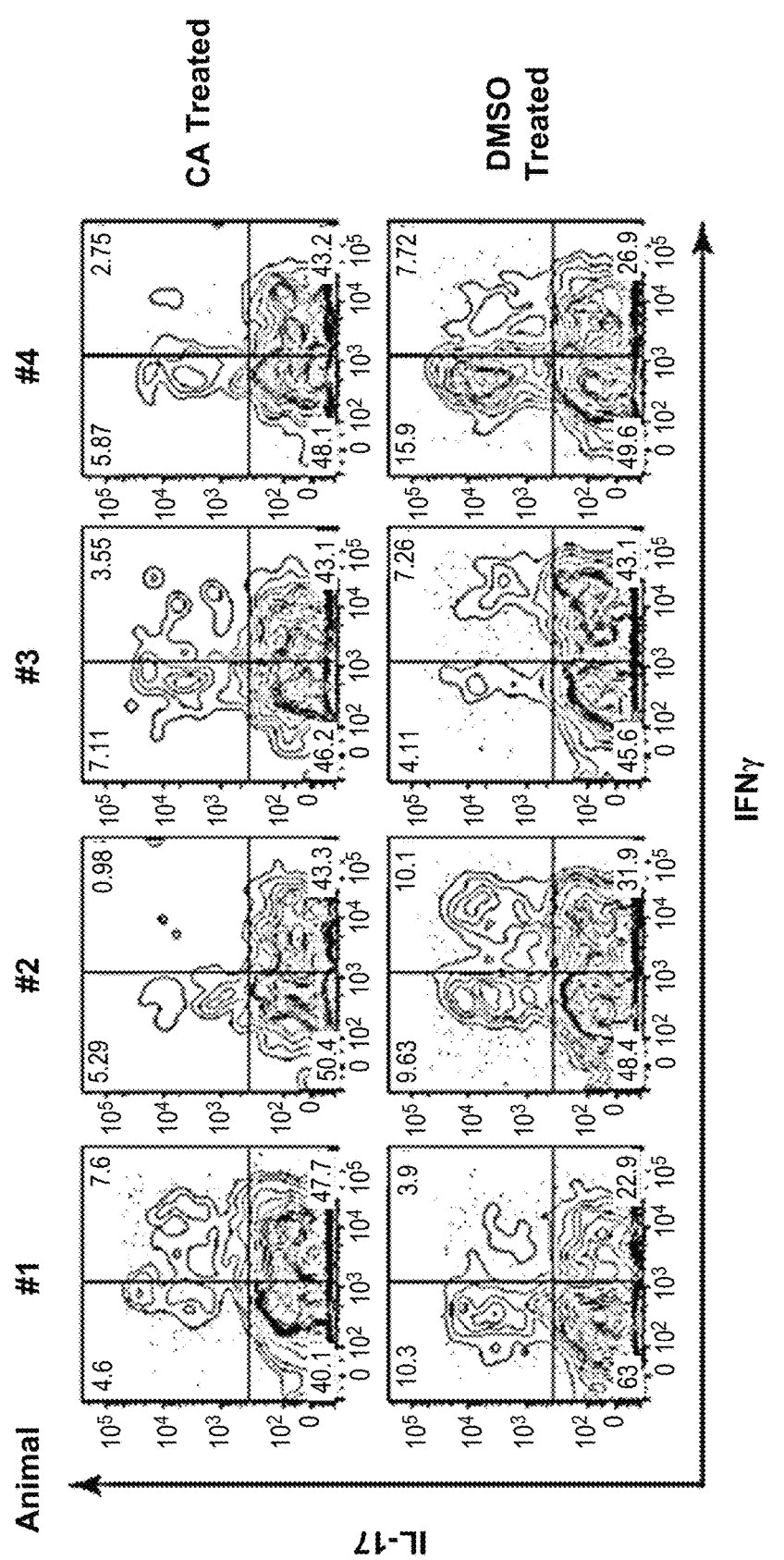
Figure 10B:
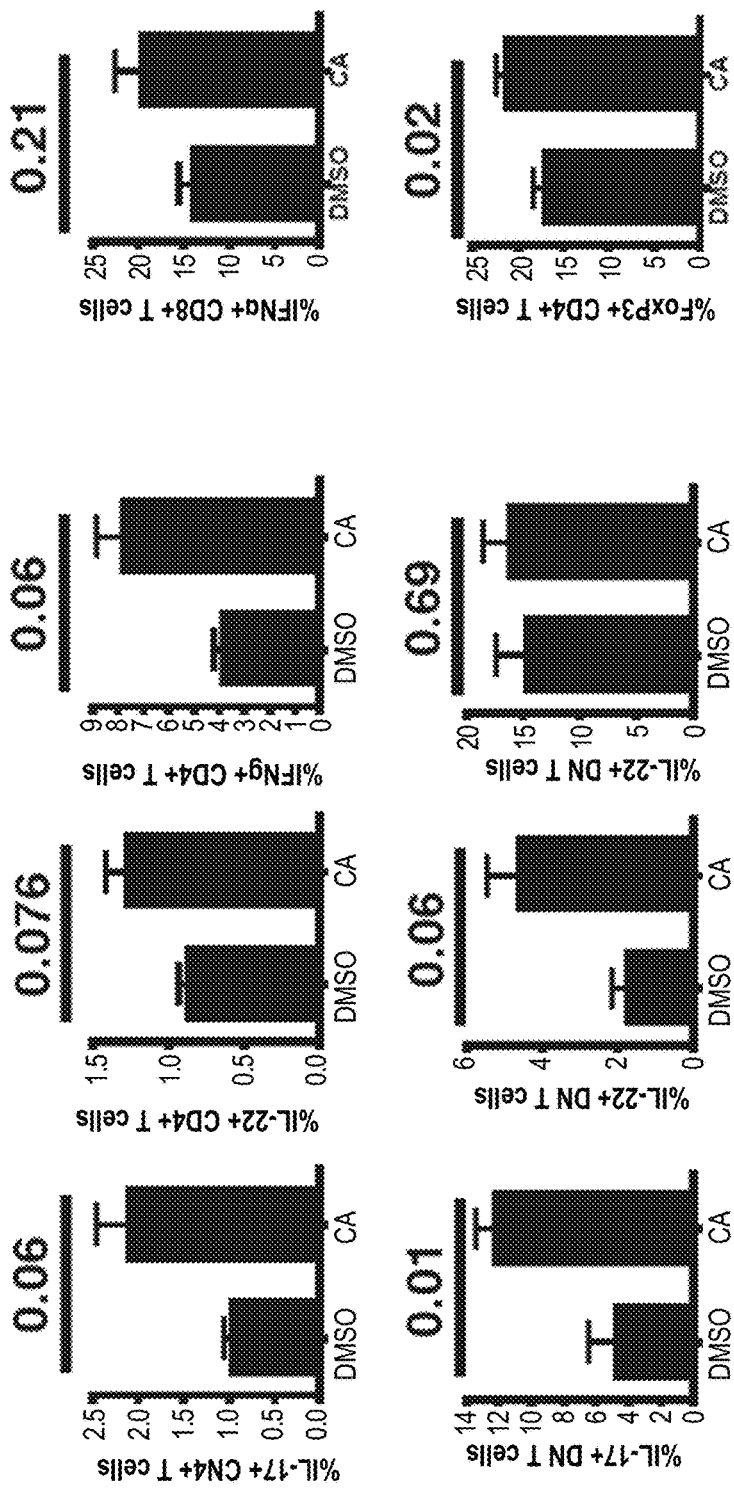
Figure 10B:
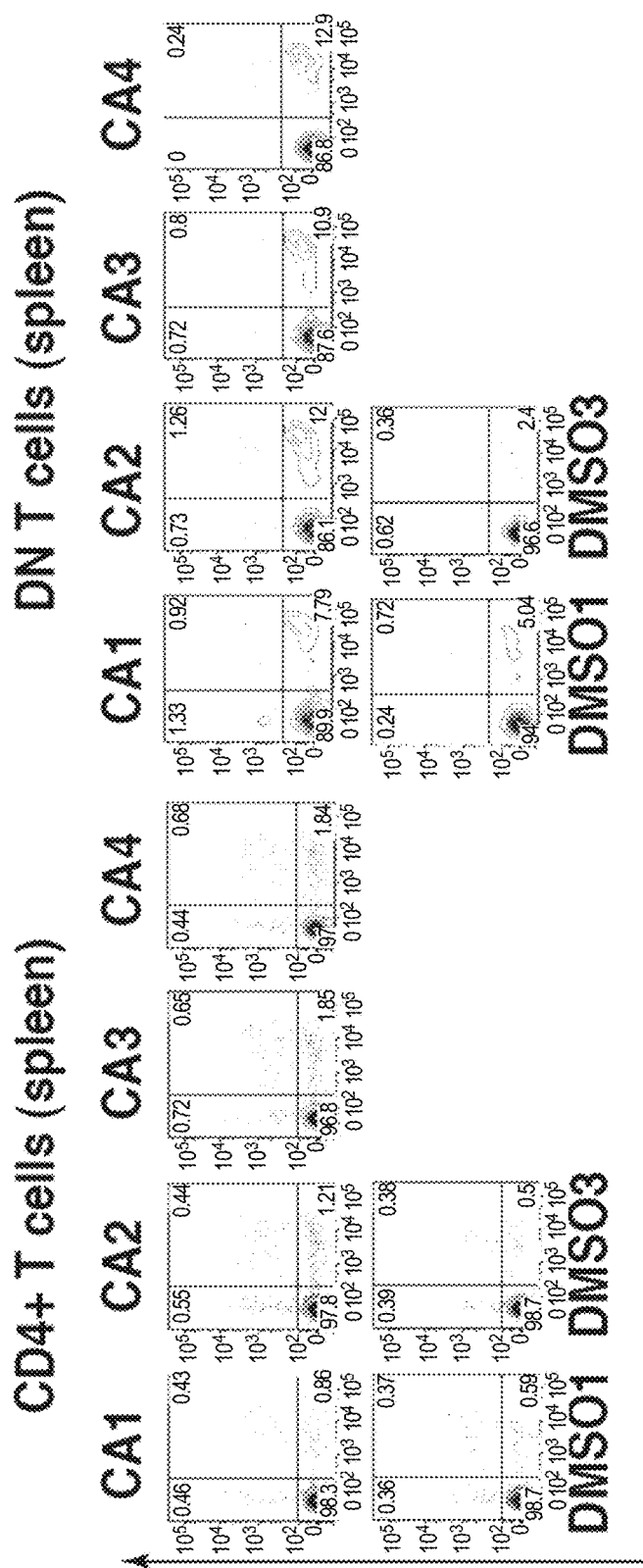

IDO and the various metabolites generated by IDO have been found to have potent immunosuppressive properties in numerous settings. In particular, 3,4 DAA has been found to abrogate the development of experimental autoimmune encephalomyelitis (EAE) in mice, and treatment of mice with 3,4 DAA and 3-HKA induced similar cytokine profiles (25). Our in vitro findings suggest that 3,4 DAA and CA may have opposing affects on immune responses, not unlike what has been reported for AHR ligands TCDD and FICZ. In EAE, TCDD was found to be protective by inducing Foxp3+ Treg cells, whereas FICZ increased disease severity by promoting the differentiation of Th17 cells, many of which also produced IL-22 (15). However, TCDD and FICZ are both known AHR agonists, like CA, whereas 3,4 DAA appears to act as an antagonist. Therefore the regulation of the Th17/Th22/Treg cell differentiation pathways at the level of the AHR is likely to be more complex than merely reflecting the presence of an agonistic or antagonistic ligand. To assess whether CA was protective in EAE we performed a series of experiments in which CA was administered in a single dose (1 mg/mouse) contained within the emulsion used to induce disease. In 4/4 experiments we found that this treatment resulted in a significant reduction of disease occurrence and severity (FIG. 10A). We observed a greatly reduced number of infiltrating T cells in the central nervous system (CNS) as well as a decrease in the frequency of infiltrating Th17 and Th22 cells. In contrast we observed an increase in the frequency and number of Th17 and Th22 cells in the spleen, suggesting that CA did not inhibit T cell activation or differentiation in response to administration of MOG peptide and adjuvant. Additionally we found that restimulation of splenocytes with MOG peptide resulted in a significantly greater amount of proliferation from CA treated mice further demonstrating that no defect in T cell activation was noted in CA treated mice. We also observed a slight, but significant, increase in Foxp3+ Treg cells in the spleen (but not in the CNS) (FIG. 10B). In sum, we find that a single administration of CA could almost completely block the development of EAE in mice and that this inhibition was associated with a dramatic reduction in the number of T cells present in the CNS as well as a reduction in the frequency of Th17 and Th22 cells in the CNS, but not in the periphery. These findings suggest that CA might represent an excellent therapeutic agent in that it suppressed autoimmunity in the absence of global immunosuppression.

Discussion

Here we have identified CA as an endogenous ligand of the AHR that is directly involved in modulating the immune response and is conserved across species. The regulation of the generation of CA, in relation to the metabolism of 3-HAA to PA or QA, is not completely understood. There are descriptions of enzymatic pathways that can result in the generation of CA from 3-HAA including the enzymes ceruloplasmin (32), superoxide dismutase (33), cinnabarinate synthase (34), and the fungal virulence factor laccase (35). It is likely that CA could also be generated through non-enzymatic reactions that would occur under oxidizing conditions (36), such as those that arise during inflammatory responses. In this regard it is interesting that reactive oxygen species (ROS) generated by neutrophils were found to be critical for IDO activation during pathogenic fungal infections in a mouse model of chronic granulomatous disease (CGD) (10). In this report, ROS were ascribed an essential role in the generation of superoxide, which is a co-factor for IDO and thus acts upstream of 3-HAA. However, it is likely that ROS generated by phagocytes could also impact the metabolism of 3-HAA, potentially leading to an increase in the generation of CA. Although ROS have typically been regarded as harmful byproducts of inflammation, there is growing evidence that they may also play a protective role in many autoimmune diseases (37). Mutations in the gene encoding p47-phox (NCF1), which regulates oxidative burst in neutrophils, lead to the spontaneous generation of rheumatoid arthritis (RA) (38) and exacerbate EAE in mice due to elevated frequencies of autoreactive T cells (39). Neutrophils have been found to express high levels of IDO in the setting of fungal infections, and it is possible that co-expression of IDO and enzymes involved in generating ROS would strongly favor the generation of CA over PA or QA (10).

It is intriguing to hypothesize that CA may act as an alternative pathway that regulates the inflammatory response, or the damage inflicted as a result of inflammation, through activation of the AHR. It is known that AHR−/− mice show elevated levels of inflammation in response to environmental pollutants suggesting that the AHR is an anti-inflammatory pathway. The generation of Th22 cells in response to AHR activation is congruent with this hypothesis. Although IL-22 was initially linked to IL-17 as a pro-inflammatory cytokine, recent evidence suggests that it probably plays an anti-inflammatory role on non-hematopoietic cells, including the regulation of epithelial cell homeostasis in the mucosal tissues. Thus the pathways that lead to the generation of CA may operate in tandem with the already described immunosuppressive mechanisms linked to tryptophan metabolism to help generate a population of Th22 cells which may play a specific role in tissue repair following inflammation.

Both IDO and the AHR pathway are highly conserved across evolution. The identification of CA as downstream metabolite of IDO capable of binding the AHR provides one of the first examples of an evolutionarily conserved pathway capable of generating an endogenous AHR ligand. These findings allow for future investigation into the potential roles that CA may play in numerous biological settings in which the AHR is involved. Furthermore, we believe that therapeutic strategies targeting the generation of CA, or involving the direct administration of CA, may prove useful in a variety of settings ranging from cancer to autoimmune disease.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

BIBLIOGRAPHY

1. Uyttenhove, C. et al. Evidence for a tumoral immune resistance mechanism based on tryptophan degradation by indoleamine 2,3 dioxygenase. *Nature Med.* 9, 1269-1274 (2003)
2. Hayashi, T. et al. Inhibition of experimental asthma by indoleamine 2,3-dioxygenase. *J. Clin. Invest.* 114, 270-279 (2004)
3. Hayashi, T. et al. Enhancement of innate immunity against *mycobacterium avium* infection by immunostimulatory DNA is mediated by indoleamine 2,3-dioxygenase. *Infect. Immun.* 69, 6156-6164 (2001)
4. Munn, D. H. et al. Prevention of allogeneic fetal rejection by tryptophan catabolism. *Science.* 281, 1191-1193 (1998)
5. Mellor, A. L., Munn, D. H. IDO expression by dendritic cells: tolerance and tryptophan catabolism. *Nat. Rev. Immunol.* 4, 762-774 (2004)
6. Munn, D. H. et al. GCN2 kinase in T cells mediates proliferative arrest and anergy induction in response to indoleamine 2,3-dioxygenase. *Immunity.* 22, 633-642 (2005).
7. Terness, P. et al. Inhibition of allogeneic T cell proliferation by indoleamine 2,3-dioxygenase-expressing dendritic cells: mediation of suppression by tryptophan metabolites. *J. Exp. Med.* 196, 447-457 (2002)
8. Fallarino, F. et al. T cell apoptosis by tryptophan catabolism. *Cell Death Diff.* 9, 1069-1077 (2002)
9. Hayashi, T. et al. 3-Hydroxyanthranilic acid inhibits PDK1 activation and suppresses experimental asthma by inducing T cell apoptosis. *Proc. Natl. Acad. Sci. USA* 104, 18619-18624 (2007)

10. Romani, L. et al. Defective tryptophan catabolism underlies inflammation in mouse chronic granulomatous disease. *Nature.* 451, 211-215 (2008)
11. Romani, L., Zelante, T., De Luca, A., Fallarino, F., Puccetti, P. IL-17 and therapeutic kynurenines in pathogenic inflammation to fungi. *J. Immunol.* 180, 5157-5162 (2008)
12. Bettelli, E. Reciprocal developmental pathways for the generation of pathogenic effector TH17 and regulatory T cells. *Nature.* 441, 235-238 (2006)
13. Mangan, P. R. et al. Transforming growth factor-β induces development of the $T_H17$ lineage. *Nature.* 441, 231-234 (2006)
14. Mucida, D. et al. Reciprocal $T_H17$ and regulatory T cell differentiation mediated by retinoic acid. *Science.* 317, 256-260 (2007)
15. Quintana, F. J. et al. Control of T(reg) and T(H)17 cell differentiation by the aryl hydrocarbon receptor. *Nature.* 453, 65-71 (2008)
16. Veldhoen, M. et al. The aryl hydrocarbon receptor links TH17-cell-mediated autoimmunity to environmental toxins. *Nature.* 453, 106-109 (2008)
17. Denison, M. S., Nagy, S. R. Activation of the aryl hydrocarbon receptor by structurally diverse exogenous and endogenous chemicals. *Annu. Rev. Pharmacol. Toxicol.* 43, 309-334 (2003)
18. Veldhoen, M., Hirota, K., Christensen, J. O'Garra, A., Stockinger, B. Natural agonists for aryl hydrocarbon receptor in culture medium are essential for optimal differentiation of Th17 cells. *J. Exp. Med.* 206, 43-49 (2009)
19. Trifari, S., Kaplan, C. D., Tran, E. H., Crellin, N. K., Spits, H. Identification of a human helper T cell population that has abundant production of interleukin 22 and is distinct from T(H)-17, T(H)1, and T(H)2 cells. *Nat. Immunol.* 10, 864-871 (2009)
20. Karchner, S. I., Franks, D. G., Kennedy, S. W., and Hahn, M. E. The molecular basis for differential dioxin sensitivity in birds: Role of the aryl hydrocarbon receptor. *Proc Natl Acad Sci USA.* 103, 6252-6257 (2006)
21. Nagy, S. R., Sanborn, J. R., Hammock, B. D., Denison, M. S. Development of a green fluorescent protein-based cell bioassay for the rapid and inexpensive detection and characterization of AH receptor agonists. *Toxicol Sci.* 65, 200-210 (2002)
22. Saito, K. et al. 4-Chloro-3-hydroxyanthranilate, 6-chlorotryptophan and norharmane attenuate quinolinic acid formation by interferon-gamma-stimulated monocytes (THP-1 cells). *Biochem. J.* 291, 11-14 (1993)
23. Heyes, M. P., Chen, C. Y., Major, E. O., Saito, K. Different kynurenine pathway enzymes limit quinolinic acid formation by various human cell types. *Biochem. J.* 326, 351-356 (1997)
24. Christen, S., Southwell-Keely, P. T., Stocker, R. Oxidation of 3-hydroxyanthranilic acid to the phenoxazinone cinnabarinic acid by peroxyl radicals and by compound I of peroxidases or catalase. *Biochemistry.* 31, 8090-8097 (1992)
25. Hiramatsu, R. et al. Cinnabarinic acid generated from 3-hydroxyanthranilic acid strongly induces apoptosis in thymocytes through the generation of reactive oxygen species and the induction of caspase. *J. Cell. Biochem.* 103, 42-53 (2008)
26. Silverstone, A. E., Frazier, D. E. Jr, Fiore, N. C., Soults, J. A., Gasiewicz, T. A. Dexamethasone, beta-estradiol, and 2,3,7,8-tetrachlorodibenzo-p-dioxin elicit thymic atrophy through different cellular targets. *Toxicol. Appl. Pharmacol.* 126, 248-259 (1994)
27. Kamath, A. B., Nagarkatti, P. S., Nagarkatti, M. Characterization of phenotypic alterations induced by 2,3,7,8-tetrachlorodibenzo-p-dioxin on thymocytes in vivo and effect on apoptosis. *Toxicol. Appl. Pharmacol.* 150, 117-124 (1998)
28. Besteman, E. G., Zimmerman, K. L., Holladay, S. D. Tetrachlorodibezno-p-dioxin (TCDD) inhibits differentiation and increases apoptotic cell death of precursor T-cells in the fetal mouse thymus. *J. Immunotoxicol.* 2, 107-114 (2005)
29. Nagai, H., Kubo, M., Abe, R., Yamamoto, M., Nohara, K. Constitutive activation of the aryl hydrocarbon receptor in T-lineage cells induces thymus involution independently of the Fas/Fas ligand signaling pathway. *Int. Immunopharmacol.* 6, 279-286 (2006)
30. Platten, M. et al. Treatment of autoimmune neuroinflammation with a synthetic tryptophan metabolite. *Science.* 310, 850-855 (2005)
31. Hori, S., Nomura, T., Sakaguchi, S. Control of regulatory T cell development by the transcription factor Foxp3. *Science.* 299, 1057-1061 (2003)
32. Eggert, C., Temp, U., Dean, J. F., Eriksson, K. E. Laccase-mediated formation of the phenoxazinone derivative, cinnabarinic acid. *FEBS Lett.* 376, 202-206 (1995)
33. Dykens, J. A., Sullivan, S. G., Stern, A. Oxidative reactivity of the tryptophan metabolites 3-hydroxyanthranilate, cinnabarinate, quinolate, and picolinate. *Bichem. Pharmacol.* 36, 211-217 (1987)
34. Rao, P. V., Vaidyanahan, C. S. Enzymatic conversion of 3-hydroxyanthranilic acid into cinnabarinic acid. Partial purification and properties of rat-liver cinnabarinate synthase. *Biochem. J.* 99, 317-322 (1966)
35. Eggert, C. Laccase-catalyzed formation of cinnabarinic acid is responsible for antibacterial activity of *Pcynoporus cinnabarinus*. *Microbiol. Res.* 152, 315-318 (1997)
36. Manthcy, M. K., Pync, S. G., Truscott, R. J. Mechanism of reaction of 3-hydroxyanthranilic acid with molecular oxygen. *Biochim. Biophys. Acta.* 1034, 207-212 (1990)
37. Gelderman, K. A. et al. Rheumatoid arthritis: the role of reactive oxygen species in disease development and therapeutic strategies. *Antioxid. Redox. Signal.* 9, 1541-1567 (2007)
38. Olofsson, P. et al. Positional identification of Ncf1 as a gene that regulates arthritis severity in rats. *Nat. Genet.* 33, 25-32 (2003)
39. Hultqvist, M. et al. Enhanced autoimmunity, arthritis, and encephalomyelitis in mice with reduced oxidative burst due to a mutation in the Ncf1 gene. *Proc. Natl. Acad. Sci. USA.* 101, 12646-12651 (2004)

What is claimed is:

1. A method of treating a subject having an autoimmune disorder selected from the group consisting of multiple sclerosis, allergic encephalomyelitis, and chronic active hepatitis, the method comprising:
administering to the subject a pharmaceutical composition comprising a compound having the structure:

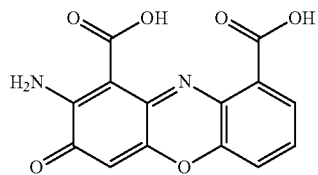 [SMILES: Nc1c(C(=O)O)c2nc3c(C(=O)O)cccc3oc-2cc1=O]

wherein the pharmaceutical composition further comprises a pharmaceutically acceptable excipient, and wherein the pharmaceutical composition is administered in an amount that induces IL-22 expression in the subject, thereby treating the subject.

2. The method of claim 1, wherein the subject is a human.

3. The method of claim 1, wherein the subject has an autoimmune disorder and wherein the autoimmune disorder is multiple sclerosis.

4. The method of claim 1, wherein the subject has an autoimmune disorder and wherein the autoimmune disorder is chronic active hepatitis.

5. The method of claim 1, wherein IL-22 expression is induced in lymphocytes.

6. The method of claim 5, wherein IL-22 expression is induced in $CD4^+$ T cells.

7. The method of claim 1, wherein the subject has an autoimmune disorder and wherein the autoimmune disorder is allergic encephalomyelitis.

* * * * *